US006331526B1

(12) United States Patent
Baserga et al.

(10) Patent No.: US 6,331,526 B1
(45) Date of Patent: *Dec. 18, 2001

(54) METHOD OF INHIBITING THE PROLIFERATION AND CAUSING THE DIFFERENTIATION OF CELLS WITH IGF-1 RECEPTOR ANTISENSE OLIGONUCLEOTIDES

(75) Inventors: Renato Baserga, Ardmore; Christian Sell, Philadelphia; Raphael Rubin, Penn Valley, all of PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/389,855

(22) Filed: Sep. 2, 1999

Related U.S. Application Data

(60) Division of application No. 08/880,313, filed on Jun. 20, 1997, now Pat. No. 6,274,562, which is a continuation of application No. 08/479,173, filed on Jun. 6, 1995, now Pat. No. 5,643,788, which is a continuation of application No. 08/158,761, filed on Nov. 30, 1993, now abandoned, which is a continuation-in-part of application No. 08/037,257, filed on Mar. 26, 1993, now abandoned.

(51) Int. Cl.[7] .............................. A61K 48/00; C12Q 1/68; C07H 21/04

(52) U.S. Cl. .................... 514/44; 536/23.1; 536/24.1; 536/24.5; 435/6

(58) Field of Search .................... 536/23.1, 24.1, 536/24.5; 514/44; 435/6

(56) References Cited

U.S. PATENT DOCUMENTS 5,271,941   12/1993   Cho-Chung .

FOREIGN PATENT DOCUMENTS

WO 93/20691   10/1993   (WO) .

OTHER PUBLICATIONS

Andrea D. Branch, A Good Antisense Molecule is Hard to Find, Feb. 1998, pp. 45–50.*
Agrawal et al., "Antisense Oligunucleotide Based Therapeutic Approach: From Laboratory to Clinical Trials, Antisense Therapy," *Efficacy and Delivery of Antisense and Ribozyme Oligonucleotides*, Feb. 23–25, 1995.
Arad et al., "Use of reconstituted Sendai virus envelopes for fusion–mediated microinjection of double–stranded RNA: inhibition of protein synthesis in interferon–treated cells", *Biochem. Biophy. Acta.*, 1986, 859, 88–94.
Baker, J. et al., "Role of Insulin–like Growth Factors in Embryonic and Postnatal Growth", *Cell*, 1993, 75, 73–82.
Baron–Van Euvrooren et al., *J. Neurosci. Res.*, 1991, 2, 244–253 (abstract).

Baserga and Rubin, "Cell Cycle and Growth Control", *Crit. Rev. Eukaryot. Gene Expr.*, 1993, 3, 47–61.
Baserga, *Cancer Res.*, 1995, 55, 249–252.
Bayever et al., *Hematological Oncology*, 1994, 12, 9–14.
Becker et al., "Proliferation of human malignant melanomas is inhibited by antisense oligodeoxynucleotides targeted against basic fibroblast growth factor", *EMBO J.*, 1992, 8(12), 3685–3691.
Brown, "Gene Therapy 'Oversold' By Researchers, Jounalists", *Washington Post*, Dec. 8, 1995, pp. 1 and A22.
Chomczynski et al., *Anal. Biochem.*, 1987, 162, 156–159.
Coghlan, *New Scientist*, 1995, 14–15.
Craig et al., *Cell*, 16, 575–588.
Culver et al., *TIG*, 1994, 10(5), 174–178.
de Fabritiis et al., *Leukemia*, 1995, 9(4), 662–664.
Dzau et al., *TIBTECH*, 1993, 11.
Feinberg et al., *Anal. Biochem.*, 1983, 132, 6–13.
Floros et al., *Exp. Cell Res.*, 1981, 132, 215–223.
Der Marderosian, A.H., "Biotechnology and Drugs," in *Remington's Pharmaceutical Sciences*, 18th Edition, Gennaro (ed.), 1990, Ch. 74, 1416–1431.
Goldring and Goldring,"Cytokines and Cell Growth Control", *Crit. Rev. Eukaryot. Gene Expr.*, 1991, 1, 301–326.
Gritz et al., *Gene*, 1983, 25, 179–188.
Gura, *Science*, 1995, 270, 575–577.
Hijiya et al., *Proc. Natl. Acad. Sci. USA*, 1994, 91, 4499–4503.
Holt et al., *Proc. Natl. Acad. Sci. USA*, 1986, 83, 4794–4798.
Hug et al., *Biochimica et Biophysica Acta*, 1991, 1097, 1–17.
Jat et al., *Mol. Cell Biol.*, 1989, 9(4), 1672–1681.
Kaleko, M. et al., "Overexpression of the Human Insulinlike Growth Factor I Receptor Promotes Ligand–Dependent Neoplastic Transformation", *Mol. Cell. Biol.*, 1990, 10, 464–473.
Lammers et al., *EMBO J.*, 1989, 8(5), 1369–1375.
Lipson et al., *Proc. Natl. Acad. Sci. USA*, 1989, 86, 9774–9777.
Liu et al., *Cell*, 1993, 75, 59–72.
Loke et al., *Curr. Topics in Microbiol. Immunol.*, 1988, 141, 282–289.
Long, L. et al., "Loss of the Metastatic Phenotype in Murine Carcinoma Cells Expressing an Antisense RNA to the Insulin–like Growth Factor Receptor[1]", *Cancer Res.*, 1995, 55, 1006–1009.

(List continued on next page.)

Primary Examiner—Sean McGarry
(74) Attorney, Agent, or Firm—Woodcock Washbun Kurtz Mackiewicz & Norris LLP

(57) ABSTRACT

A method of inhibiting the proliferation and causing the differentiation of undifferentiated cells comprising contacting the undifferentiated cells with an effective amount of an antisense oligonucleotide having a sequence which is complementary to a region of the IGF-1 receptor RNA. The sequence of the antisense oligonucleotide is selected from an oligodeoxynucleotide sequence complementary to codons −29 to −24 of the signal sequence of the IGF-1 receptor and an oligoribonucleotide sequence complementary to codons 1 to 309 of the sequence of the IGF-1 receptor. The oligoribonucleotide sequence may be provided by an expression vector.

21 Claims, 12 Drawing Sheets

OTHER PUBLICATIONS

McCaulay, *Br. J. Cancer*, 1992, 65, 311–320.

McCubrey, J.A. et al., "Growth–Promoting Effects of Insulin–Like Growth Factor–1(IGF–1) on Hematopoietic Cells: Overexpression of Introduced IGF–1 Receptor Abrogates Interleukin–3 Dependency of Murine Factor–Dependent Cells by a Ligand–Dependent Mechanism", *Blood*, 1991, 78, 921–929.

Marks et al., *Mol. Endocrinol.*, 1991, 5(8), 1158–1168.

Mercola et al., *Biochem. Biophys. Res. Commun.*, 1987, 147(1), 288–294.

Milligan et al., *J. Med. Chem.*, 1993, 36(14), 1923–1937.

Nabel et al., *Proc. Natl. Acad. Sci. USA*, 1993, 90, 11307–11311.

Pietrzkowski et al., *Cancer Res.*, 1992, 52, 6447–6451.

Porcu et al., *Mol. Cell. Biol.*, 1992, 12(11), 5069–5077.

Radna et al., *Mol. Cell. Biol.*, 1989, 9, 3093–3096.

Rappolee et al., *J. Cell Biochem.*, 1989, 39, 1–11.

Ratajczak et al., "Oligonucleotide Therapeutics for Human Leukemia, Antisense Therapy," *Efficacy and Delivery of Antisense and Ribozome Oligonucleotide*, presented Feb. 23–24, 1995, 1–11.

Reiss et al., *Oncogene*, 1992, 7, 2243–2248.

Resnick–Silverman et al., *J. Virol.*, 1991, 65, 2845–2852.

Resnicoff et al., "The Insulin–like Growth Factor I Receptor Protects Tumor Cells from Apoptosis in Vivo", *Cancer Res.*, 1995, 55, 2463–2469.

Resnicoff, M., et al., "Growth Inhibition of Human Melanoma Cells in Nude Mice by Antisense Strategies to the Type 1 Insulin–like Growth Factor Receptor", *Cancer Res.*, 1994, 54, 4848–4850.

Sell et al., "Simian virus 40 large tumor antigen is unable to transform mouse embryonic fibroblasts lacking type 1 insulin–like growth factor receptor", *Proc. Natl. Acad. Sci. USA*, 1993, 90, 11217–11221.

Shen et al., *Mol. Cell Biol.*, 1982, 2(9), 1145–1154.

Skorski et al., *Proc. Natl. Acad. Sci. USA*, 1994, 91, 4504–4508.

Stein, C. et al., "Antisense oligonucleotides as Therapeutic Agents—Is the Bullet Really Magical", *Science*, 1993, 261, 1004–1012.

Stein, *J. Cell Physiol.*, 1979, 99, 43–54.

Surmacz et al., "The role of IGF1 receptor in regulation of cdc2 mRNA levels in fibroblasts," *Exp. Cell Res.*, 1992, 199, 275–278.

Talavera et al., *Cancer Res.*, 1990, 50, 3019–3024.

Tegtmeyer, *J. Virol.*, 1975, 15(3), 613–618.

Thomas, *Methods Enzymol.*, 1983, 100, 255–266.

Thompson et al., *Virology*, 1990, 178, 15–34.

Todaro et al., *J. Cell Biol.*, 1963, 17, 299–313.

Trojan et al., *J. Cell Biol.*, 1991, 115(3 Part 2), 263a.

Trojan, J. et al., "Loss of tumorogenicity of rat glioblastoma directed by episome–based antisense cDNA transcription of insulin–like growth factor I", *Proc. Natl. Acad. Sci. USA*, 1992, 89, 4874–4878.

Trojan et al., "Treatment and Prevention of Rat Gliobastoma by Immunogenic C6 Cells Expressing Antisense Insulin–Like Growth Factor I RNA", *Science*, 1993, 259, 94–97.

Tseng et al., "Antisense oligonucleotide technology in the development of cancer therapeutics", *Cancer Gene Therapy*, 1994, 1(1), 65–71.

Uhlmann, E. et al., "Antisense Oligonucleotides: A New Therapeutic Principle", *Chem. Rev.*, 1990, 90(4), 543–584.

Ullrich, A. et al., "Insulin–Like Growth Factor I Receptor Primary Structure: Comparison with Insulin Receptor Suggests Structural Determinants that Define Functional Specificity", *EMBO J.*, 1986, 5(10), 2503–2512.

Weiss, R., "Upping the Antisense Ante, Scientists Bet on Profits from Reverse Genetics", *Science News*, 1991, 139, 108–109.

Westermann, P. et al., "Inhibition of Expression of SV40 Virus Large T–Antigen by Antisense Oligodeoxyribonucleotides", *Biomedica Biochimica Acta*, 1989, 48(1), 85–93.

Wetmur, J., "DNA Probes: Applications of the Principles of Nucleic Acid Hybridization", *Crit. Rev. Biochem. And Molecular Biol.*, 1991, 26(3/4), 227–259.

Wharton et al., *Cell Growth and Division*, 1989, 10, 139–153.

Yamori et al., *Cancer Res.*, 1991, 5859–5865.

Lahm, H. et al., "Growth Inhibition of Human Colorectal Carcinomas by a Monoclonal Antibody Directed Against the IGF–1 Receptor," *Eur. J. Cancer*, 1991, 27(Suppl. 3), Abstract No. 11.053.

Pietrzkowski, Z. et al., "Roles of Insulinlike Growth Factor 1 (IGF–1) and the IGF–1 Receptor in Epidermal Growth Factor–Stimulated Growth of 3T3 Cells", *Mol. Cell. Biol.*, 1992, 12(9), 3883–3889.

Pietrzykowski, Z. et al., "Constitutive Expression of Insulin– like Growth Factor 1 and Insulin–like Growth Factor 1 Rceptor Abrogates All Requirements for Exogenous Growth Factors", *Cell Growth & Diff.*, 1992, 3, 199–205.

Pietrzykowski, Z. et al., "Inhibition of Growth of Prostatic Cancer Cell Lines by Peptide Analogues on Insulin–like Growth Factor 1," *Cancer Res.*, 1993, 53, 1102–1106.

Pietrzykowski, Z. et al., "Autocrine Growth of Cells Overexpressing the Human IGF–1 and IGF–1 Receptor Genes," *Federal of American Society for Experimental Biology*, 75th Annual Meeting, Atlanta, GA, 1991, Part 3, Abstract No. 7268.

Rohlik, Q. et al., "An Antibody to the Receptor for Insulin–like Growth Factor 1 Inhibits the Growth of MCF–7 Cells in Tissue Culture," *Biochem. Biophys. Res. Commun.*, 1987, 149(1), 276–281.

Shapiro, D. N. et al., "Antisense–mediated reduction in insulin–like growth factor–1 receptor expression suppresses the malignant phenotype of a human rhabdomyosarcoma," *Cancer Res.*, Eighty–Third Annual Meeting, 1992, 33, Abstract No. 2112.

Wickstrom, E. et al., "Antisense DNA Methylphosphonate Inhibition of C–MYC Gene Expression in Transgenic Mice," *FASEB J.*, 75th Annual Meeting, Atlanta, GA, 1991, Part 2, Abstract No. 6218.

\* cited by examiner

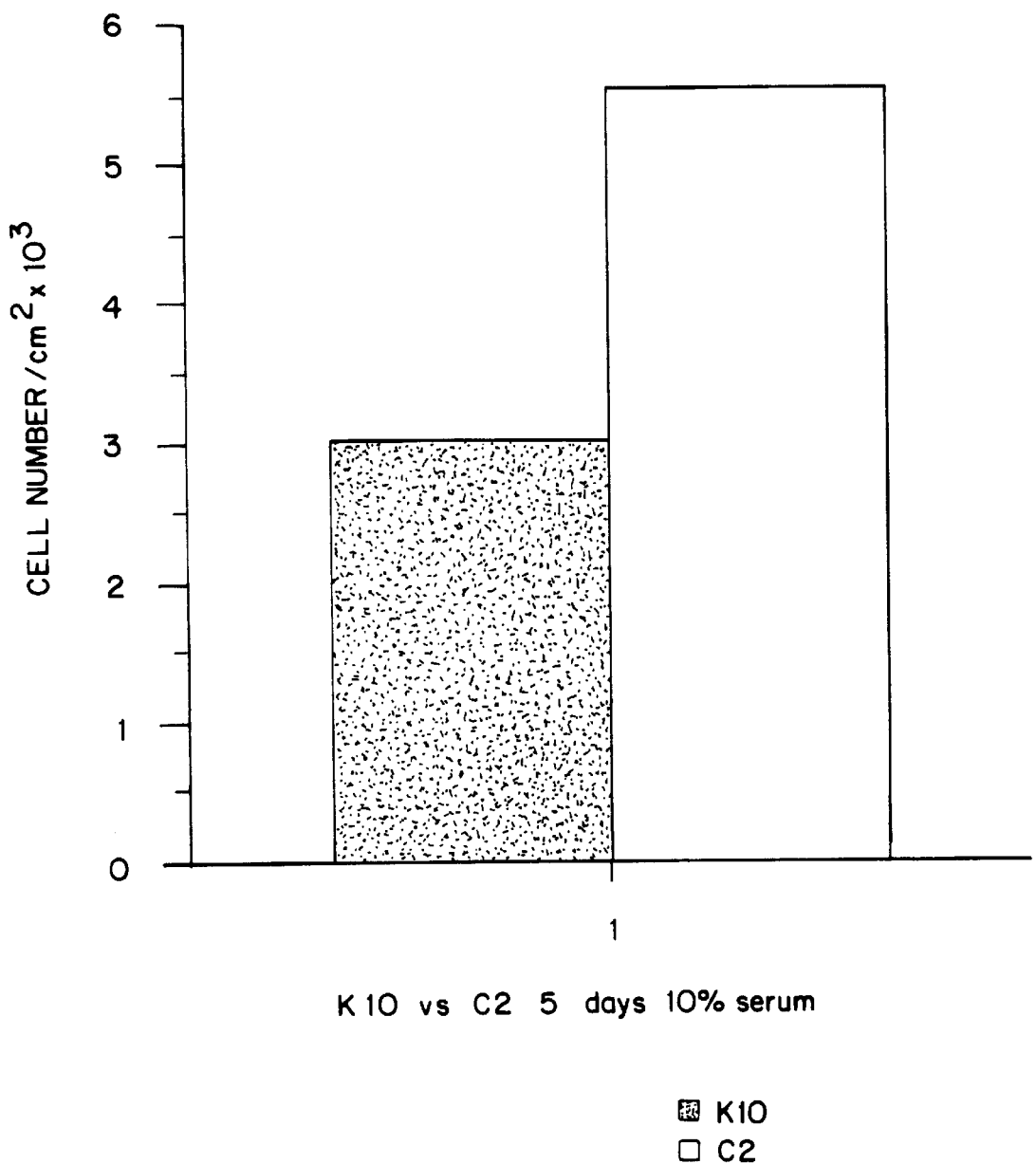

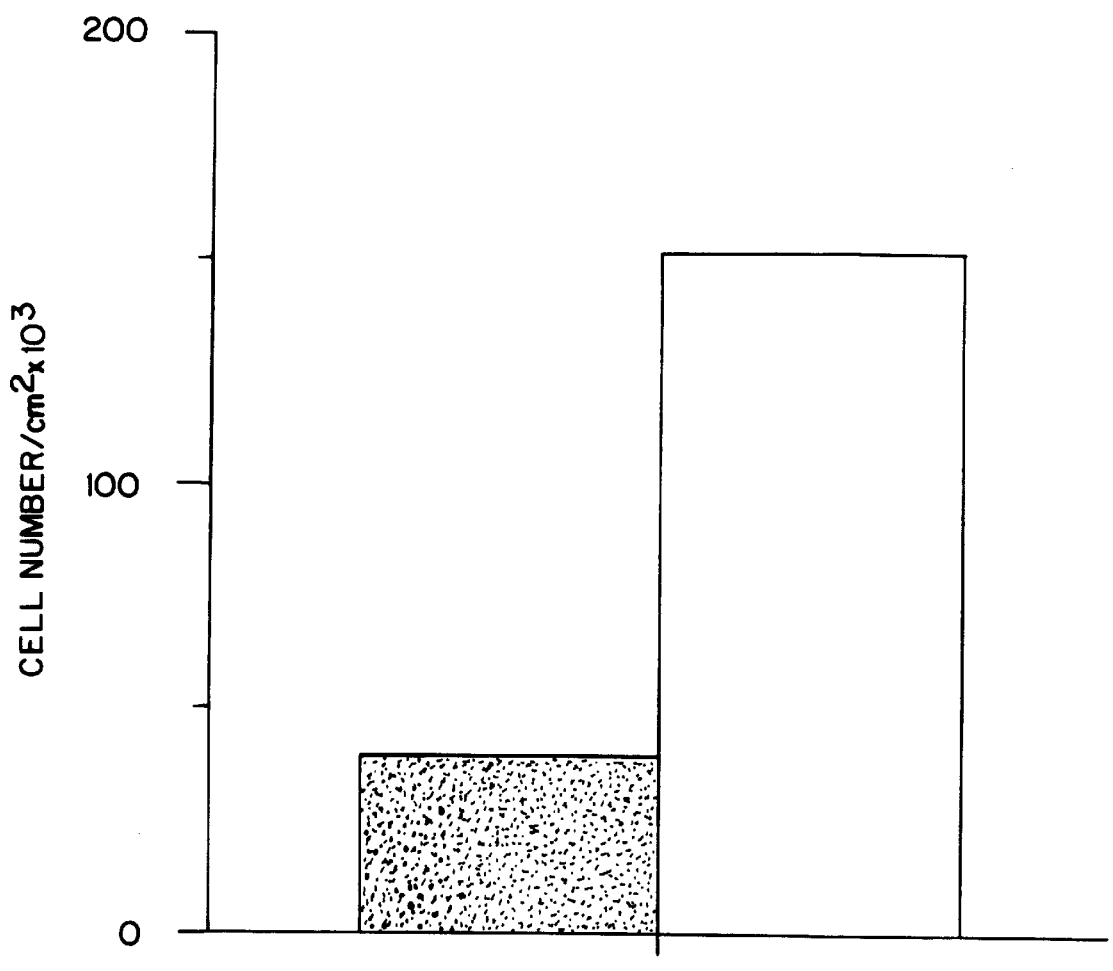

```
TTTTTTTTTTTGAGAAAAGGGAATTTCATCCCAAATAAAAGGAGGATGAAGTCTGGCTCCGGAGGAGGGTCCCCG
                                            MetLysSerGlyGlyGlySerPro
                                            -30
          -20                                 -10                              -1  1     → α subunit
ThrSerLeuTrpGlyLeuLeuPheLeuSerAlaAlaLeuSerLeuTrpProThrSerGlyGluIleCysGlyPro
ACCTCGCTGTGGGGGCTCCTGTTTCTCTCCGCGGCTCTCCGCTCTGGCCGACGAGTGGAGAAATCTGCGGGCCA                150

GlyIleAspIleArgAsnAspTyrGlnIleLeuLysArgLeuGluAsnCysThrValIleGluGlyTyrLeuHis
GGCATCGACATCCGCAACGACTATCAGATCCTGAAGCGCCTGGAGAACTGCACGGTGATCGAGGGCTACCTCCAC
        10                        20                        30

IleLeuIleLeuIleSerLysAlaGluAspTyrArgSerTyrArgPheProLysLeuThrValIleThrGluTyrLeu
ATCCTGCTACTCATCTCCAAGGCCGAGGACTACCGCAGCTACCGCTTCCCCAAGCTTACGGTCATCACCGAGTACTTG         300
                    40               ─①─                        50

LeuLeuPheArgValAlaAlaGlyLeuSerLeuLeuGlyAspLeuPheProAsnLeuThrValIleArgGlyTrpLys
CTGCTGTTCCGAGTGGCCGCTGGCCTGAGCCTCCTGGGGGACCTCTTCCCCAACCTCACGGTCATCCGCGGCTGGAAA
        60                        70                        80

LeuPheTyrAsnTyrAlaLeuValIleGluPheGluMetThrAsnLeuLysAspIleGlyLeuTyrAsnLeuArgAsn
CTCTTCTACAACTACGCCCTGGTCATCTTCGAGATGACCAATCTCAAGGATATTGGGCTTTACAACCTGAGGAAC             450
        90                        100                       130

IleThrArgGlyAlaIleArgGluIleLysAsnAlaAspLeuCysTyrLeuSerThrValAspTrpSerLeuIle
ATTACTCGGGGGGCCATCAGGATTGAGAAAAATGCTGACCTGTGTTACCTCTCCACTGTGGACTGGTCCCTGATC
        110                       120                       130

LeuAspAlaValSerAsnTyrIleValGlyLysAsnLysAsnProProLysGluCysGlyAspLeuCysProGlyThr
CTGGATGCGGTGTCCAATTACATTGTGGGGAATAAGCCCCCCAAAGGAATGTGGGGACCTGTCCAGGGACC                 600
        140                       150

MetGluGluLysProMetCysGluLysThrThrIleAsnAsnGluTyrAsnTyrArgCysTrpThrThrAsnArg
ATGGAGGAGAAGCCGATGTGTGAGAAGACCACCATCAACAATGAGTACAACTACCGCTGCTGGACCACAAACCGC
        160                       170                       180
```

FIG. 7A

```
         190                    200
CysGlnLysMetCysProSerThrCysGlyLysArgAlaCysThrGluAsnAsnGluCysCysHisProGluCys
TGCCAGAAAATGTGCCCAAGCACGTGTGGGAAGGCGGGCGTGCACCGAGAACAATGAGTGCTGCCACCCCGAGTGC    750
                                                            230
LeuGlySerCysSerAlaProAspAsnAspThrAlaCysValAlaArgHisTyrTyrTyrAlaGlyValCys
CTGGGCAGCTGCAGCGCCCCTGACAACGACACGGCCTGTGTAGCTCGCCACTACTACTATGCCGGTGTCTGT
                   220

ValProAlaCysProProAsnThrTyrArgCysValAspArgAspPheCysMetGlnGluCysProSerGly
GTGCCTGCCTGCCCGCCCAACACCTACAGGTGTGTGGACCGTGACTTCTGCATGCAGGAGTGCCCCTCGGGC    900
                  240                     250                  280
LeuSerAlaGluSerSerAspGlyGluPheValIleHisAspGlyGluCysIleProCysIleProValCysGluGlu
CTCAGCGCCGAGAGCAGCGACGGCGAGTTTGTGATCCACGACGGGGAGTGCATCCCTGCATGCCCCGTGTGTGAGGAGAAA   1050
                   260              270                     300
PheIleArgArgAsnGlySerGlnSerMetTyrCysIleProCysCysLysProValCysGluGlu
TTCATCCGCAGGAACGGGCAGCCAGAGCATGTACTGCATCCCTTGCTGTAAGCCTGTGTGTGAGGAAGAA
                290                              330
LysLysThrIleAspSerValThrSerAlaGlnMetLeuGlnGlyLysThrIlePheLysGlyAsnLeu
AAGAAAACAATTGATTCTGTTACTTCTGCTCAGATGCTCCAAGGAATGACCATCTTCAAGGGCAATTTG
      310                     320
LeuIleAsnIleArgArgGlyAsnAsnIleAlaSerGluLeuLeuAsnPheMetGlyLeuIleGluValValThr
CTCATTAACATCCGACGGGGAATAACATTGCTTCAGAGCTGGAGAACTTCATGGGGCTCATCGAGGTGGTGACG    1200
        340                         380
GlyTyrValLysIleArgHisSerHisAlaLeuValSerPheLeuLysAsnLeuArgLeuLeuGly
GGCTACGTGAAGATCCGCCATTCTCATGCCCTTGTCTCCTTCCTAAAAAACCTTCGCCTCATCCTAGGA
                  360              370

GluGlnLeuGluGlyTyrSerPheTyrValLeuAspAsnGlnAsnLeuGlnLeuTrpAspTrpAsp
GAGGAGCAGCTAGAAGGGGAATTACTCCCTTTCTACGTCCTGGACAACCAGAACTTGCAGCAACTGTGGGACTGGGAC    1350
                                    400
```

FIG. 7B

```
     410                   420                    430
HisArgAsnLeuThrIleLysAlaGlyLysMetTyrPheAlaPheAsnProLysLeuCysValSerGluIleTyr
CACCGCAACCTGACCATCAAAGCAGGAAAATGTACTTTGCTTTCAATCCCAAATTATGTTTCCGAAATTTAC
                      440                      450
ArgMetGluGluValThrGlyThrLysGlyArgGlnSerLysAspIleAsnThrArgAsnAsnGlyGluArg         1500
CGGATGGAGGAAGTGACGGGGACTAAAGGGCGCCAAAGCAAGGACATAAACACCAGGAACAACGGGGAGAGA
      460                470                     480
AlaSerCysGluSerAspValLeuHisPheThrSerThrThrSerLysAsnArgIleIleIleThrTrpHis
GCCTCCTGTGAAAGTGACGTCCTGCATTTCACCTCGACCACCAGTAAGAATCGCATCATCATAACCTGGCAC
                       490                      500
ArgTyrArgProAspTyrArgAspLeuIleSerPheThrValTyrTyrLysGluAlaProPheLysAsnVal
CGGTACCGGCCCGACTACAGGGATCTCATCAGTTTCACCGTTTACTACAAGGAAGCACCCTTTAAGAATGTC
     510                   520                     530                    1650
ThrGluTyrAspGlyGlnAspAlaCysGlySerAsnSerTrpAsnMetValAspLeuProProAsnLys
ACAGAGTATGATGGCCAGGATGCCTGCGGGTCCAACAGCTGGAACATGGTGGACCTCCCGCCCAACAAG
                     540                     550
AspValGluProGlyIleLeuLeuHisAspHisIleArgGlyLeuLysLysProTrpThrGlnTyrAlaValLysValValAlaValThr
GACGTGGAGCCCGGCATCTTACTACACGACCATATCCGTGGGCTGAAGAAGCCCTGGACTCAGTACGCCGTTGTACGTCGTGTGACC
      560                     570                     580
LeuThrMetValGluAsnAspHisIleArgGlyLeuLysLysProTrpThrGlnTyrAlaValLysSerVal         1800
CTCACCATGGTGGAGAACGACCATATCCGTGGGCTGAAGAAGCCCTGGACTCAGTACGCCGTTAAGTCAGTT
                      590                      600
ProSerIleProLeuAspValLeuSerAlaSerAsnSerSerGlnLeuIleLeuValLysTrpAsnProProSer
CCTTCCATTCCCTTGGACGTTCTTTCAGCATCGAACTCCTCTCAGTTAATCGTGAAGTGGAACCCCTCCCTCT
      610                     620                      630
LeuProAsnGlyAsnLeuSerTyrTyrIleValArgTrpGlnArgGlnProGlnAspGlyTyrLeuTyrArgHis         1950
CTGCCCAACGGCAACCTGAGTTACTACATTGTGCGCTGGCAGCGGCAGCCTCAGGACGGCTACCTTTACCGGCAC
```

```
                                                                                          880
          860                              870
ArgLysTyrGlyGlyAlaLysLeuAsnArgLeuAsnProGlyAsnTyrThrAlaArgIleGlnAlaThrSerLeu
AGGAAGTATGGAGGGCAAGCTAAACCGGCTAAACCCGGGAACTACACAGCCCGGATTCAGGCCACATCTCTC
                                                                                                    2850
                                      890                                         900
          SerGlyAsnGlySerTrpThrAspProValPhePheTyrValGlnAlaAlaLysThrGlyTyrGluAsnPheIleHis
          TCTGGGAATGGGTCGTGGACAGATCCTGTGTCTTCTATGTCCAGGCCGCAAAAACAGGATATGAAACTTCATCCAT
                  910                                        920                                      930
LeuIleIleAlaAlaLeuProValAlaValLeuLeuIleAlaValGlyLeuValIleMetLeuTyrValPheHisArg
CTGATCATCGCTCTGCCCGTCGCTGTCCTGCTTATCGCTGTGGGAGGGTTGGTCATTATGCTTACGTCTTCCATAGA
                                                                                              3000
                   940                                    950
LysArgAsnAsnSerArgLeuGlyAsnGlyValLeuTyrAlaSerValAsnProGluTyrPheSerAlaAlaAsp
AAGAGAAATAACAGCAGGCTGGGGAATGGAGTCCTGTATGCCTCTGTGAACCCGGAGTACTTCAGCGCTGCTGAT
                           960                                         970                                  980
ValTyrValProAspGluTrpGluValAlaAlaArgGluLysIleThrMetSerArgGluLeuGlyGlnGlySerPhe
GTGTACGTTCCTGATGAGTGGGAGGTGGCTGCTCGGGAGAGAAGATCACCATGAGCCGGGAACTTGGGCAGGGTCGTTT
               990                                    1000
GlyMetValTyrGluGlyValAlaLysGlyValValAlaLysAspGlyProGluThrArgValAlaIleLysThrVal
GGGATGGTCTATGAAGGAGTTGCCAAGGGTGTGGTAGCAAAGGATGGACCAGAGACCAGAGTGGCCATTAAAACAGTG
                                                                                              3150
                    1010                                    1020                                    1030
AsnGluAlaAlaSerMetArgGluArgIleGluPheLeuAsnGluAlaSerValMetLysGluPheAsnCysHis
AACGAGGCCGCAAGCATGCGTGAGAGGATTGAGTTTCTCAACGAAGCTTCTGTGATGAAGGAGTTCAATTGTCAC
                   1040                                   1050
HisValValArgLeuLeuGlyValValSerGlnGlyGlnProThrLeuValIleMetGluLeuMetThrArgGly
CATGTGGTGCGATTGCTGGGTGTGGTGTCCCAAGGCCAGCCCACACTGGTCATCATGGAACTGATGACACGGGGC
                                                                                              3300
            1060                                     1070                                   1080
AspLeuLysSerTyrLeuArgSerLeuArgProGluMetGluAsnAsnProValLeuAlaProProSerLeuSer
GATCTCAAAAGTTATCTCCGGTCTCTGAGGCCAGAAATGGAGAATAATCCAGTCCTAGCACCTCCAAGCCTGAGC
```

FIG. 7E

```
                                                                                                    1100
            LysMetIleGlnMetAlaGlyGluIleAlaAspGlyMetAlaTyrLeuAsnAlaAsnLysPheValHisArgAsp
            AAGATGATTCAGATGGCCGGAGAGATTGCAGACGGCATGGCATACCTCAACGCCAATAAGTTCGTCCACAGAGAC       3450
                                                                                1130
               1110
            LeuAlaAlaArgAsnCysMetValAlaGluAspPheThrValLysIleGlyAspPheGlyMetThrArgAspIle
            CTTGCTGCCCGGAATTGCATGGTAGCGGAAGATTTCACAGTCAAAATCGGAGATTTTGGTATGACGCGAGATATC
                      1140                                                            1150
            TyrGluThrAspTyrTyrArgLysGlyLysGlyLeuLeuProValArgTrpMetSerProGluSerLeuLys
            TATGAGACAGACTATTACCGGAAAGGAGGGAAAGGGCTGCCCGTGCCTGGATGTCTCCTGAGTCCCTCAAG       3600
                                                                              1180
                     1160                                       1170
            AspGlyValPheThrThrTyrSerAspValTrpSerPheGlyValValLeuTrpGluIleAlaThrLeuAlaGlu
            GATGGAGTCTTCACCACTTACTCGGACGTCTGGTCTTTCGGGGTCGTCCTCTGGGAGATCGCCACACTGGCCGAG
                                                                                     1230
                     1190                                      1200
            GlnProTyrGlnGlyLeuSerAsnGluGlnValLeuArgPheValMetGluGlyGlyLeuLeuAspLysProAsp
            CAGCCCTACCAGGGCCTTGTCCAACGAGCAAGTCCTTCGCTTCGTCATGGAGGGCGGCCTTCTGGACAAGCCAGAC       3750
                                                                                    1230
                    1210                                     1220
            AsnCysProAspMetLeuPheGluLeuMetArgMetCysTrpGlnTyrAsnProLysMetArgProSerPheLeu
            AACTGTCCTGACATGCTGTTTGAACTGATGCGCATGTGCTGGCAGTATAACCCCAAGATGAGGCCTTCCTTCCTG
                     1240                                    1250
            GluIleIleSerSerIleLysGluGluMetGluProGlyPheArgGluValSerPheTyrTyrSerGluGluAsn
            GAGATCATCAGCAGCATCAAAGAGGAGATGGAGCCTGGCTTCCGGGAGGTCTCCTTCTACTACAGCGAGGAGAAC       3900
                                                                                  1280
                    1260                                   1270
            LysLeuProGluProGluGluLeuAspLeuGluProGluAsnMetGluSerValProLeuAspProSerAlaSer
            AAGCTGCCCGAGCCGGAGGAGCTGGACCTGGAGCCAGAGAACATGGAGAGCGTCCCCCTGGACCCCTCGGCTCC
                     1290                                  1300
            SerSerSerLeuProAspArgHisSerGlyHisLysAlaGluAsnGlyProGlyValLeuVal
            TCGTCCTCCCTGCCCGACCGCCACTCAGGACACACTTAAGGCCGAGAACGGCCCCGGGCCCTGGGGTGCTGGTC       4050
```

FIG. 7F

```
                    1310                                   1320                                    1330
LeuArgAlaSerPheAspGluArgGlnProTyrAlaHisMetAsnGluArgArgLysAsnGluArgArgAlaLeuPro
CTCCGGGCCAGCTTTGACCGTCGCCAGCCTTACGCCCACATGAACGAAAGGAGGAAGAACGAGCGGGCCTTGCCG                    4200

LeuProGlnSerSerThrThrCysEnd
CTGCCCCAGTCTTCGACCACCTGCTGATCCTTGGATCCTGTGCAAACAGTAACGTGTGCGCACGCGCAGCGG                       4350
GGTGGGGGGAGAGAGTTTTAACAATCCATTCACAAGCCTCCTGTACCTCAGTGGATCTTCAGTTCTGCCCT
TGCTGCCCGCGGAGACAGCTTCTCTGCAGTAAAACACATTTGGGATGTTCCTTTTTCAATATGCAAGCAGCTT                      4500
TTTATTCCCTGCCCAAACCCTTAACTGACATGGGCCTTTAAGAACCTTAATGACAACACTTAATAGCAACAGAGC
ACTTGAGAACCAGTCTCCTCACTCTGTCCCCTTCTCTCCCTTCTCTCTCCCTGTTCCCTGTCCCTGTGGCCCC                      4650
GGAAAAATAATTGCCACAAGTCCAGCTGGGAAGCCCTTTTATCAGTTTGAGGAAGTGGCTGTCCCTGTGGCCCC
ATCCAACCACTGTACACACCCGCCTGGGTCATTACAAAAAAACACGTTCATCCAAGGCTGTTACCATTTAACGC                    4800
TTATCTTTCACCTTTCTAGGGACATGAAATTTCTCCCTGAACTTTCTCCATTTGAGAGACACGCTCTCATTGCTTCCGGAGGCATGGG      4800
TGAGCATGGGCAGGTGGTTGCTCCATTTGAGAGACACGCTCTCATTGCTTCCGGAGGCATGGG
GCTGCTCAAGGCCACAGGCACACAGGTCTCATTGCTTCTGACTAGATTATTATTTGGGGAACTGGACACAATAG                    4950
GTCTTTCTCTCAGTGAAGGTGGGGAGAAGCTGAACCGGC                                                        4989
```

FIG. 7G

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Other Information: PCR amplimer

<400> SEQUENCE: 1
accattgatt ctgttacttc                                              20

<210> SEQ ID NO 2
<211> LENGTH: 20
<212> TYPE: DNA
<213> ORGANISM: Artificial Sequence
<220> FEATURE:
<223> OTHER INFORMATION: Other Information: PCR amplimer

<400> SEQUENCE: 2
atactctgtg acattcttaa                                              20

<210> SEQ ID NO 3
<211> LENGTH: 20
<212> TYPE: DNA
<213> ORGANISM: Artificial Sequence
<220> FEATURE:
<223> OTHER INFORMATION: Other Information: probe

<400> SEQUENCE: 3
ctgctcctct cctaggatga                                              20

<210> SEQ ID NO 4
<211> LENGTH: 18
<212> TYPE: DNA
<213> ORGANISM: Artificial Sequence
<220> FEATURE:
<223> OTHER INFORMATION: Other Information: antisense to -29 to -24 of
      IGF-1R

<400> SEQUENCE: 4
tcctccggag ccagactt                                                18

<210> SEQ ID NO 5
<211> LENGTH: 18
<212> TYPE: DNA
<213> ORGANISM: Artificial Sequence
<220> FEATURE:
<223> OTHER INFORMATION: Other Information: sense to -29 to -24 of
```

IGF-1R

<400> SEQUENCE: 5
aagtctggct ccggagga                                              18

<210> SEQ ID NO 6
<211> LENGTH: 20
<212> TYPE: DNA
<213> ORGANISM: Artificial Sequence
<220> FEATURE:
<223> OTHER INFORMATION: Other Information: mismatched oligonucleotide

<400> SEQUENCE: 6
gcaccgggaa gttgtgtcaa                                            20

<210> SEQ ID NO 7
<211> LENGTH: 927
<212> TYPE: DNA
<213> ORGANISM: Artificial Sequence
<220> FEATURE:
<223> OTHER INFORMATION: Other Information: codons 1-309 of IGF-1R

<400> SEQUENCE: 7
gaaatctgcg ggccaggcat cgacatccgc aacgactatc agcagctgaa           50
gcgcctggag aactgcacgg tgatcgaggg ctacctccac atcctgctca          100
tctccaaggc cgaggactac cgcagctacc gcttccccaa gctcacggtc          150
attaccgagt acttgctgct gttccgagtg gctggcctcg agagcctcgg          200
agacctcttc cccaacctca cggtcatccg cggctggaaa ctcttctaca          250
actacgccct ggtcatcttc gagatgacca atctcaagga tattgggctt          300
tacaacctga ggaacattac tcggggggcc atcaggattg agaaaaatgc          350
tgacctctgt tacctctcca ctgtggactg gtccctgatc ctggatgcgg          400
tgtccaataa ctacattgtg gggaataagc cccaaaagga atgtgggac           450 ctgtgtccag ggaccatgga ggagaagccg atgtgtgaga agaccaccat          500
caacaatgag tacaactacc gctgctggac cacaaaccgc tgccagaaaa          550
tgtgcccaag cacgtgtggg aagcgggcgt gcaccgagaa caatgagtgc          600
tgccaccccg agtgcctggg cagctgcagc gcgcctgaca acgacacggc          650
ctgtgtagct gccgccact actactatgc cggtgtctgt gtgcctgcct           700
gcccgcccaa cacctacagg tttgagggct ggcgctgtgt ggaccgtgac          750
ttctgcgcca acatcctcag cgccgagagc agcgactccg aggggtttgt          800
gatccacgac ggcgagtgca tgcaggagtg ccccctcggc ttcatccgca          850
acggcagcca gagcatgtac tgcatcccct gtgaaggtcc ttgcccgaag          900
gtctgtgagg aagaaaagaa aacaaag                                   927

<210> SEQ ID NO 8
<211> LENGTH: 927
<212> TYPE: DNA
<213> ORGANISM: Artificial Sequence
<220> FEATURE:
<223> OTHER INFORMATION: Other Information: antisense to codons 1-309 of
      IGF-1R

<400> SEQUENCE: 8
ctttgttttc ttttcttcct cacagacctt cgggcaagga ccttcacaag           50

-continued

| | |
|---|---|
| ggatgcagta catgctctgg ctgccgttgc ggatgaagcc cgaggggcac | 100 |
| tcctgcatgc actcgccgtc gtggatcaca aaccccctcgg agtcgctgct | 150 |
| ctcggcgctg aggatgttgg cgcagaagtc acggtccaca cagcgccagc | 200 |
| cctcaaacct gtaggtgttg ggcgggcagg caggcacaca gacaccggca | 250 |
| tagtagtagt ggcggcaagc tacacaggcc gtgtcgttgt caggcgcgct | 300 |
| gcagctgccc aggcactcgg ggtggcagca ctcattgttc tcggtgcacg | 350 |
| cccgcttccc acacgtgctt gggcacattt tctggcagcg gtttgtggtc | 400 |
| cagcagcggt agttgtactc attgttgatg gtggtcttct cacacatcgg | 450 |
| cttctcctcc atggtccctg gacacaggtc cccacattcc tttgggggct | 500 |
| tattccccac aatgtagtta ttggacaccg catccaggat cagggaccag | 550 |
| tccacagtgg agaggtaaca gaggtcagca ttttttcacaa tcctgatggc | 600 |
| cccccgagta atgttcctca ggttgtaaag cccaatatcc ttgagattgg | 650 |
| tcatctcgaa gatgaccagg gcgtagttgt agaagagttt ccagccgcgg | 700 |
| atgaccgtga ggttggggaa gaggtctccg aggctctcga ggccagccac | 750 |
| tcggaacagc agcaagtact cggtaatgac cgtgagcttg gggaagcggt | 800 |
| agctgcggta gtcctcggcc ttggagatga gcaggatgtg gaggtagccc | 850 |
| tcgatcaccg tgcagttctc caggcgcttc agctgctgat agtcgttgcg | 900 |
| gatgtcgatg cctggcccgc agatttc | 927 |

<210> SEQ ID NO 9
<211> LENGTH: 4989
<212> TYPE: DNA
<213> ORGANISM: Homo sapiens
<220> FEATURE:
<223> OTHER INFORMATION: Other Information: human IGF-1R sequence

<400> SEQUENCE: 9

| | |
|---|---|
| tttttttttt ttttgagaaa gggaatttca tcccaaataa aagga atg aag tct<br>                                                                                                 Met Lys Ser<br>                                                                                                  1 | 54 |
| ggc tcc gga gga ggg tcc ccg acc tcg ctg tgg ggg ctc ctg ttt<br>Gly Ser Gly Gly Gly Ser Pro Thr Ser Leu Trp Gly Leu Leu Phe<br> 5                          10                       15 | 99 |
| ctc tcc gcc gcg ctc tcg ctc tgg ccg acg agt gga gaa atc tgc<br>Leu Ser Ala Ala Leu Ser Leu Trp Pro Thr Ser Gly Glu Ile Cys<br>     20                      25                       30 | 144 |
| ggg cca ggc atc gac atc cgc aac gac tat cag cag ctg aag cgc<br>Gly Pro Gly Ile Asp Ile Arg Asn Asp Tyr Gln Gln Leu Lys Arg<br>     35                      40                       45 | 189 |
| ctg gag aac tgc acg gtg atc gag ggc tac ctc cac atc ctg ctc<br>Leu Glu Asn Cys Thr Val Ile Glu Gly Tyr Leu His Ile Leu Leu<br>    50                      55                       60 | 234 |
| atc tcc aag gcc gag gac tac cgc agc tac cgc ttc ccc aag ctc<br>Ile Ser Lys Ala Glu Asp Tyr Arg Ser Tyr Arg Phe Pro Lys Leu<br> 65                        70                       75 | 279 |
| acg gtc att acc gag tac ttg ctg ctg ttc cga gtg gct ggc ctc<br>Thr Val Ile Thr Glu Tyr Leu Leu Leu Phe Arg Val Ala Gly Leu<br>     80                      85                       90 | 324 |
| gag agc ctc gga gac ctc ttc ccc aac ctc acg gtc atc cgc ggc<br>Glu Ser Leu Gly Asp Leu Phe Pro Asn Leu Thr Val Ile Arg Gly<br>     95                     100                   105 | 369 |
| tgg aaa ctc ttc tac aac tac gcc ctg gtc atc ttc gag atg acc | 414 |

```
                                                          -continued

Trp Lys Leu Phe Tyr Asn Tyr Ala Leu Val Ile Phe Glu Met Thr
    110             115                 120 aat ctc aag gat att ggg ctt tac aac ctg agg aac att act cgg      459
Asn Leu Lys Asp Ile Gly Leu Tyr Asn Leu Arg Asn Ile Thr Arg
    125             130                 135 ggg gcc atc agg att gag aaa aat gct gac ctc tgt tac ctc tcc      504
Gly Ala Ile Arg Ile Glu Lys Asn Ala Asp Leu Cys Tyr Leu Ser
    140             145                 150 act gtg gac tgg tcc ctg atc ctg gat gcg gtg tcc aat aac tac      549
Thr Val Asp Trp Ser Leu Ile Leu Asp Ala Val Ser Asn Asn Tyr
    155             160                 165 att gtg ggg aat aag ccc cca aag gaa tgt ggg gac ctg tgt cca      594
Ile Val Gly Asn Lys Pro Pro Lys Glu Cys Gly Asp Leu Cys Pro
    170             175                 180 ggg acc atg gag gag aag ccg atg tgt gag aag acc acc atc aac      639
Gly Thr Met Glu Glu Lys Pro Met Cys Glu Lys Thr Thr Ile Asn
    185             190                 195 aat gag tac aac tac cgc tgc tgg acc aca aac cgc tgc cag aaa      684
Asn Glu Tyr Asn Tyr Arg Cys Trp Thr Thr Asn Arg Cys Gln Lys
    200             205                 210 atg tgc cca agc acg tgt ggg aag cgg gcg tgc acc gag aac aat      729
Met Cys Pro Ser Thr Cys Gly Lys Arg Ala Cys Thr Glu Asn Asn
    215             220                 225 gag tgc tgc cac ccc gag tgc ctg ggc agc tgc agc gcg cct gac      774
Glu Cys Cys His Pro Glu Cys Leu Gly Ser Cys Ser Ala Pro Asp
    230             235                 240 aac gac acg gcc tgt gta gct tgc cgc cac tac tat gcc ggt          819
Asn Asp Thr Ala Cys Val Ala Cys Arg His Tyr Tyr Tyr Ala Gly
    245             250                 255 gtc tgt gtg cct gcc tgc ccg ccc aac acc tac agg ttt gag ggc      864
Val Cys Val Pro Ala Cys Pro Pro Asn Thr Tyr Arg Phe Glu Gly
    260             265                 270 tgg cgc tgt gtg gac cgt gac ttc tgc gcc aac atc ctc agc gcc      909
Trp Arg Cys Val Asp Arg Asp Phe Cys Ala Asn Ile Leu Ser Ala
    275             280                 285 gag agc agc gac tcc gag ggg ttt gtg atc cac gac ggc gag tgc      954
Glu Ser Ser Asp Ser Glu Gly Phe Val Ile His Asp Gly Glu Cys
    290             295                 300 atg cag gag tgc ccc tcg ggc ttc atc cgc aac ggc agc cag agc      999
Met Gln Glu Cys Pro Ser Gly Phe Ile Arg Asn Gly Ser Gln Ser
    305             310                 315 atg tac tgc atc cct tgt gaa ggt cct tgc ccg aag gtc tgt gag     1044
Met Tyr Cys Ile Pro Cys Glu Gly Pro Cys Pro Lys Val Cys Glu
    320             325                 330 gaa gaa aag aaa aca aag acc att gat tct gtt act tct gct cag     1089
Glu Glu Lys Lys Thr Lys Thr Ile Asp Ser Val Thr Ser Ala Gln
    335             340                 345 atg ctc caa gga tgc acc atc ttc aag ggc aat ttg ctc att aac     1134
Met Leu Gln Gly Cys Thr Ile Phe Lys Gly Asn Leu Leu Ile Asn
    350             355                 360 atc cga cgg ggg aat aac att gct tca gag ctg gag aac ttc atg     1179
Ile Arg Arg Gly Asn Asn Ile Ala Ser Glu Leu Glu Asn Phe Met
    365             370                 375 ggg ctc atc gag gtg gtg acg ggc tac gtg aag atc cgc cat tct     1224
Gly Leu Ile Glu Val Val Thr Gly Tyr Val Lys Ile Arg His Ser
    380             385                 390 cat gcc ttg gtc tcc ttg tcc ttc cta aaa aac ctt cgc ctc atc     1269
His Ala Leu Val Ser Leu Ser Phe Leu Lys Asn Leu Arg Leu Ile
    395             400                 405
```

-continued

```
cta gga gag gag cag cta gaa ggg aat tac tcc ttc tac gtc ctc       1314
Leu Gly Glu Glu Gln Leu Glu Gly Asn Tyr Ser Phe Tyr Val Leu
    410                 415                 420 gac aac cag aac ttg cag caa ctg tgg gac tgg gac cac cgc aac       1359
Asp Asn Gln Asn Leu Gln Gln Leu Trp Asp Trp Asp His Arg Asn
425                 430                 435 ctg acc atc aaa gca ggg aaa atg tac ttt gct ttc aat ccc aaa       1404
Leu Thr Ile Lys Ala Gly Lys Met Tyr Phe Ala Phe Asn Pro Lys
    440                 445                 450 tta tgt gtt tcc gaa att tac cgc atg gag gaa gtg acg ggg act       1449
Leu Cys Val Ser Glu Ile Tyr Arg Met Glu Glu Val Thr Gly Thr
    455                 460                 465 aaa ggg cgc caa agc aaa ggg gac ata aac acc agg aac aac ggg       1494
Lys Gly Arg Gln Ser Lys Gly Asp Ile Asn Thr Arg Asn Asn Gly
470                 475                 480 gag aga gcc tcc tgt gaa agt gac gtc ctg cat ttc acc tcc acc       1539
Glu Arg Ala Ser Cys Glu Ser Asp Val Leu His Phe Thr Ser Thr
    485                 490                 495 acc acg tcg aag aat cgc atc atc ata acc tgg cac cgg tac cgg       1584
Thr Thr Ser Lys Asn Arg Ile Ile Ile Thr Trp His Arg Tyr Arg
    500                 505                 510 ccc cct gac tac agg gat ctc atc agc ttc acc gtt tac tac aag       1629
Pro Pro Asp Tyr Arg Asp Leu Ile Ser Phe Thr Val Tyr Tyr Lys
515                 520                 525 gaa gca ccc ttt aag aat gtc aca gag tat gat ggg cag gat gcc       1674
Glu Ala Pro Phe Lys Asn Val Thr Glu Tyr Asp Gly Gln Asp Ala
    530                 535                 540 tgc ggc tcc aac agc tgg aac atg gtg gac gtg gac ctc ccg ccc       1719
Cys Gly Ser Asn Ser Trp Asn Met Val Asp Val Asp Leu Pro Pro
    545                 550                 555 aac aag gac gtg gag ccc ggc atc tta cta cat ggg ctg aag ccc       1764
Asn Lys Asp Val Glu Pro Gly Ile Leu Leu His Gly Leu Lys Pro
560                 565                 570 tgg act cag tac gcc gtt tac gtc aag gct gtg acc ctc acc atg       1809
Trp Thr Gln Tyr Ala Val Tyr Val Lys Ala Val Thr Leu Thr Met
    575                 580                 585 gtg gag aac gac cat atc cgt ggg gcc aag agt gag atc ttg tac       1854
Val Glu Asn Asp His Ile Arg Gly Ala Lys Ser Glu Ile Leu Tyr
    590                 595                 600 att cgc acc aat gct tca gtt cct tcc att ccc ttg gac gtt ctt       1899
Ile Arg Thr Asn Ala Ser Val Pro Ser Ile Pro Leu Asp Val Leu
605                 610                 615 tca gca tcg aac tcc tct tct cag tta atc gtg aag tgg aac cct       1944
Ser Ala Ser Asn Ser Ser Ser Gln Leu Ile Val Lys Trp Asn Pro
    620                 625                 630 ccc tct ctg ccc aac ggc aac ctg agt tac tac att gtg cgc tgg       1989
Pro Ser Leu Pro Asn Gly Asn Leu Ser Tyr Tyr Ile Val Arg Trp
    635                 640                 645 cag cgg cag cct cag gac ggc tac ctt tac cgg cac aat tac tgc       2034
Gln Arg Gln Pro Gln Asp Gly Tyr Leu Tyr Arg His Asn Tyr Cys
650                 655                 660 tcc aaa gac aaa atc ccc atc agg aag tat gcc gac ggc acc atc       2079
Ser Lys Asp Lys Ile Pro Ile Arg Lys Tyr Ala Asp Gly Thr Ile
    665                 670                 675 gac att gag gag gtc aca gag aac ccc aag act gag gtg tgt ggt       2124
Asp Ile Glu Glu Val Thr Glu Asn Pro Lys Thr Glu Val Cys Gly
    680                 685                 690 ggg gag aaa ggg cct tgc tgc gcc tgc ccc aaa act gaa gcc gag       2169
Gly Glu Lys Gly Pro Cys Cys Ala Cys Pro Lys Thr Glu Ala Glu
695                 700                 705
```

```
aag cag gcc gag aag gag gag gct gaa tac cgc aaa gtc ttt gag       2214
Lys Gln Ala Glu Lys Glu Glu Ala Glu Tyr Arg Lys Val Phe Glu
    710                 715                 720 aat ttc ctg cac aac tcc atc ttc gtg ccc aga cct gaa agg aag       2259
Asn Phe Leu His Asn Ser Ile Phe Val Pro Arg Pro Glu Arg Lys
725                 730                 735 cgg aga gat gtc atg caa gtg gcc aac acc acc atg tcc agc cga       2304
Arg Arg Asp Val Met Gln Val Ala Asn Thr Thr Met Ser Ser Arg
        740                 745                 750 agc agg aac acc acg gcc gca gac acc tac aac atc acc gac ccg       2349
Ser Arg Asn Thr Thr Ala Ala Asp Thr Tyr Asn Ile Thr Asp Pro
    755                 760                 765 gaa gag ctg gag aca gag tac cct ttc ttt gag agc aga gtg gat       2394
Glu Glu Leu Glu Thr Glu Tyr Pro Phe Phe Glu Ser Arg Val Asp
770                 775                 780 aac aag gag aga act gtc att tct aac ctt cgg cct ttc aca ttg       2439
Asn Lys Glu Arg Thr Val Ile Ser Asn Leu Arg Pro Phe Thr Leu
        785                 790                 795 tac cgc atc gat atc cac agc tgc aac cac gag gct gag aag ctg       2484
Tyr Arg Ile Asp Ile His Ser Cys Asn His Glu Ala Glu Lys Leu
    800                 805                 810 ggc tgc agc gcc tcc aac ttc gtc ttt gca agg act atg ccc gca       2529
Gly Cys Ser Ala Ser Asn Phe Val Phe Ala Arg Thr Met Pro Ala
815                 820                 825 gaa gga gca gat gac att cct ggg cca gtg acc tgg gag cca agg       2574
Glu Gly Ala Asp Asp Ile Pro Gly Pro Val Thr Trp Glu Pro Arg
        830                 835                 840 cct gaa aac tcc atc ttt tta aag tgg ccg gaa cct gag aat ccc       2619
Pro Glu Asn Ser Ile Phe Leu Lys Trp Pro Glu Pro Glu Asn Pro
    845                 850                 855 aat gga ttg att cta atg tat gaa ata aaa tac gga tca caa gtt       2664
Asn Gly Leu Ile Leu Met Tyr Glu Ile Lys Tyr Gly Ser Gln Val
860                 865                 870 gag gat cag cga gaa tgt gtg tcc aga cag gaa tac agg aag tat       2709
Glu Asp Gln Arg Glu Cys Val Ser Arg Gln Glu Tyr Arg Lys Tyr
        875                 880                 885 gga ggg gcc aag cta aac cgg cta aac ccg ggg aac tac aca gcc       2754
Gly Gly Ala Lys Leu Asn Arg Leu Asn Pro Gly Asn Tyr Thr Ala
    890                 895                 900 cgg att cag gcc aca tct ctc tct ggg aat ggg tcg tgg aca gat       2799
Arg Ile Gln Ala Thr Ser Leu Ser Gly Asn Gly Ser Trp Thr Asp
905                 910                 915 cct gtg ttc ttc tat gtc cag gcc aaa aca gga tat gaa aac ttc       2844
Pro Val Phe Phe Tyr Val Gln Ala Lys Thr Gly Tyr Glu Asn Phe
        920                 925                 930 atc cat ctg atc atc gct ctg ccc gtc gct gtc ctg ttg atc gtg       2889
Ile His Leu Ile Ile Ala Leu Pro Val Ala Val Leu Leu Ile Val
    935                 940                 945 gga ggg ttg gtg att atg ctg tac gtc ttc cat aga aag aga aat       2934
Gly Gly Leu Val Ile Met Leu Tyr Val Phe His Arg Lys Arg Asn
950                 955                 960 aac agc agg ctg ggg aat gga gtg ctg tat gcc tct gtg aac ccg       2979
Asn Ser Arg Leu Gly Asn Gly Val Leu Tyr Ala Ser Val Asn Pro
        965                 970                 975 gag tac ttc agc gct gct gat gtg tac gtt cct gat gag tgg gag       3024
Glu Tyr Phe Ser Ala Ala Asp Val Tyr Val Pro Asp Glu Trp Glu
    980                 985                 990 gtg gct cgg gag aag atc acc atg agc cgg gaa ctt ggg cag ggg       3069
Val Ala Arg Glu Lys Ile Thr Met Ser Arg Glu Leu Gly Gln Gly
```

|  |  |
|---|---|
| tcg ttt ggg atg gtc tat gaa gga gtt gcc aag ggt gtg gtg aaa<br>Ser Phe Gly Met Val Tyr Glu Gly Val Ala Lys Gly Val Val Lys<br>1010                       1015                       1020 | 3114 |
| gat gaa cct gaa acc aga gtg gcc att aaa aca gtg aac gag gcc<br>Asp Glu Pro Glu Thr Arg Val Ala Ile Lys Thr Val Asn Glu Ala<br>1025                       1030                       1035 | 3159 |
| gca agc atg cgt gag agg att gag ttt ctc aac gaa gct tct gtg<br>Ala Ser Met Arg Glu Arg Ile Glu Phe Leu Asn Glu Ala Ser Val<br>1040                       1045                       1050 | 3204 |
| atg aag gag ttc aat tgt cac cat gtg gtg cga ttg ctg ggt gtg<br>Met Lys Glu Phe Asn Cys His His Val Val Arg Leu Leu Gly Val<br>1055                       1060                       1065 | 3249 |
| gtg tcc caa ggc cag cca aca ctg gtc atc atg gaa ctg atg aca<br>Val Ser Gln Gly Gln Pro Thr Leu Val Ile Met Glu Leu Met Thr<br>1070                       1075                       1080 | 3294 |
| cgg ggc gat ctc aaa agt tat ctc cgg tct ctg agg cca gaa atg<br>Arg Gly Asp Leu Lys Ser Tyr Leu Arg Ser Leu Arg Pro Glu Met<br>1085                       1090                       1095 | 3339 |
| gag aat aat cca gtc cta gca cct cca agc ctg agc aag atg att<br>Glu Asn Asn Pro Val Leu Ala Pro Pro Ser Leu Ser Lys Met Ile<br>1100                       1105                       1110 | 3384 |
| cag atg ggc gga gag att gca gac ggc atg gca tac ctc aac gcc<br>Gln Met Ala Gly Glu Ile Ala Asp Gly Met Ala Tyr Leu Asn Ala<br>1115                       1120                       1125 | 3429 |
| aat aag ttc gtc cac aga gac ctt gct gcc cgg aat tgc atg gta<br>Asn Lys Phe Val His Arg Asp Leu Ala Ala Arg Asn Cys Met Val<br>1130                       1135                       1140 | 3474 |
| gcc gaa gat ttc aca gtc aaa atc gga gat ttt ggt atg acg cga<br>Ala Glu Asp Phe Thr Val Lys Ile Gly Asp Phe Gly Met Thr Arg<br>1145                       1150                       1155 | 3519 |
| gat atc tat gag aca gac tat tac cgg aaa gga ggg aaa ggg ctg<br>Asp Ile Tyr Glu Thr Asp Tyr Tyr Arg Lys Gly Gly Lys Gly Leu<br>1160                       1165                       1170 | 3564 |
| ctg ccc gtg cgc tgg atg tct cct gag tcc ctc aag gat gga gtc<br>Leu Pro Val Arg Trp Met Ser Pro Glu Ser Leu Lys Asp Gly Val<br>1175                       1180                       1185 | 3609 |
| ttc acc act tac tcg gac gtc tgg tcc ttc ggg gtc gtc ctc tgg<br>Phe Thr Thr Tyr Ser Asp Val Trp Ser Phe Gly Val Val Leu Trp<br>1190                       1195                       1200 | 3654 |
| gag atc gcc aca ctg gcc gag cag ccc tac cag ggc ttg tcc aac<br>Glu Ile Ala Thr Leu Ala Glu Gln Pro Tyr Gln Gly Leu Ser Asn<br>1205                       1210                       1215 | 3699 |
| gag caa gtc ctt cgc ttc gtc atg gag ggc ggc ctt ctg gac aag<br>Glu Gln Val Leu Arg Phe Val Met Glu Gly Gly Leu Leu Asp Lys<br>1220                       1225                       1230 | 3744 |
| cca gac aac tgt cct gac atg ctg ttt gaa ctg atg cgc atg tgc<br>Pro Asp Asn Cys Pro Asp Met Leu Phe Glu Leu Met Arg Met Cys<br>1235                       1240                       1245 | 3789 |
| tgg cag tat aac ccc aag atg agg cct tcc ttc ctg gag atc atc<br>Trp Gln Tyr Asn Pro Lys Met Arg Pro Ser Phe Leu Glu Ile Ile<br>1250                       1255                       1260 | 3834 |
| agc agc atc aaa gag gag atg gag cct ggc ttc cgg gag gtc tcc<br>Ser Ser Ile Lys Glu Glu Met Glu Pro Gly Phe Arg Glu Val Ser<br>1265                       1270                       1275 | 3879 |
| ttc tac tac agc gag gag aac aag ctg ccc gag ccg gag gag ctg<br>Phe Tyr Tyr Ser Glu Glu Asn Lys Leu Pro Glu Pro Glu Glu Leu<br>1280                       1285                       1290 | 3924 |
| gac ctg gag cca gag aac atg gag agc gtc ccc ctg gac ccc tcg | 3969 |

-continued

```
Asp Leu Glu Pro Glu Asn Met Glu Ser Val Pro Leu Asp Pro Ser
    1295                1300                1305 gcc tcc tcg tcc tcc ctg cca ctg ccc gac aga cac tca gga cac          4014
Ala Ser Ser Ser Ser Leu Pro Leu Pro Asp Arg His Ser Gly His
    1310                1315                1320 aag gcc gag aac ggc ccc ggc cct ggg gtg ctg gtc ctc cgc gcc          4059
Lys Ala Glu Asn Gly Pro Gly Pro Gly Val Leu Val Leu Arg Ala
    1325                1330                1335 agc ttc gac gag aga cag cct tac gcc cac atg aac ggg ggc cgc          4104
Ser Phe Asp Glu Arg Gln Pro Tyr Ala His Met Asn Gly Gly Arg
    1340                1345                1350 aag aac gag cgg gcc ttg ccg ctg ccc cag tct tcg acc tgc tga          4149
Lys Asn Glu Arg Ala Leu Pro Leu Pro Gln Ser Ser Thr Cys
    1355                1360                1365 tccttggatc ctgaatctgt gcaaacagta acgtgtgcgc acgcgcagcg               4199
gggtgggggg ggagagagag ttttaacaat ccattcacaa gcctcctgta               4249
cctcagtgga tcttcagttc tgcccttgct gcccgcggga gacagcttct               4299
ctgcagtaaa acacatttgg gatgttcctt ttttcaatat gcaagcagct               4349
ttttattccc tgcccaaacc cttaactgac atgggccttt aagaacctta               4399 atgacaaac ttaatagcaa cagagcactt gagaaccagt ctcctcactc                4449
tgtccctgtc cttccctgtt ctccctttct ctctcctctc tgcttcataa               4499
cggaaaaata attgccacaa gtccagctgg gaagcccttt ttatcagttt               4549
gaggaagtgg ctgtccctgt ggcccatcc caccactgta cacaccgcc                 4599 tgacaccgtg ggtcattaca aaaaaacacg tggagatgaa aattttacc                4649 tttatctttc acctttctag ggacatgaaa tttacaaagg gccatcgttc               4699
atccaaggct gttaccattt taacgctgcc taattttgcc aaaatcctga               4749
actttctccc tcatcggccc ggcgctgatt cctcgtgtcc ggaggcatgg               4799
gtgagcatgg cagctggttg ctccatttga gagacacgct ggcgacacac               4849
tccgtccatc cgactgcccc tgctgtgctg ctcaaggcca caggcacaca               4899
ggtctcaatg cttctgacta gattattatt tgggggaact ggacacaata               4949
ggtctttctc tcagtgaagg tggggagaag ctgaaccggc                          4989
```

METHOD OF INHIBITING THE PROLIFERATION AND CAUSING THE DIFFERENTIATION OF CELLS WITH IGF-1 RECEPTOR ANTISENSE OLIGONUCLEOTIDES

REFERENCE TO RELATED APPLICATIONS

This application is a divisional of U.S. provisional Application Serial No. 08/880,313, filed Jun. 20, 1997 now U.S. Pat. No. 6,274,562 which is a continuation of Ser. No. 08/479,173, filed Jun. 6, 1995 now U.S. Pat. No. 5,643,788, which is a continuation of Ser. No. 08/158,761 filed Nov. 30, 1993 and now abandoned, which is a continuation-in-part of Ser. No. 08/037,257 filed Mar. 26, 1993 and now abandoned, each of which is incorporated herein by reference in its entirety.

INTRODUCTION

This invention was funded by National Institute of Health Grants GM 33694 and CA 56309. The U.S. government may have certain rights in the invention.

BACKGROUND OF THE INVENTION

The IGF-1 receptor is expressed in many cell types including fibroblasts, epithelial cells, smooth muscle cells, chondrocytes, osteoblasts and several lineages of hemopoietic cells which have IGF-1 receptors and an absolute requirement for IGF-1 for growth in cultures. A review of human cells expressing the IGF-1 receptor and requiring IGF-1 for growth can be found in Baserga and Rubin, Critical Reviews in Eukaryote Gene Expression, 1993, 3: 47–61; and Goldring and Goldring, Eukaryote Gene Expression 1991, 1, 301–326. Macaulay, Br. J. Cancer 1992, 65, 311–320, has reviewed the expression of insulin-like growth factors (both IGF-1 and IGF-2) and their receptors in human cancer. Recently, it was shown that IGF-1 peptide analogs may be useful for inhibiting the growth of IGF-1 dependent cells (Pietrzkowski et al., Cancer Res. 1993, 53, 1102–1106). Antisense oligonucleotides to mRNA coding for IGF-1 was used to transform rat glioblastoma cells. The cells reversed the transformed phenotype, and acted immunogenic against the parent glioblastoma cell line, completely inhibiting its growth. Tojan et al. Science, 1993, 259, 94–97 and Trojan et al., Proc. Natl. Acad. Sci. U.S.A., 1992, 89, 4874–4878. However, effective methods of inhibiting growth and causing differentiation of cells are still greatly desired.

SUMMARY OF THE INVENTION

Methods of inhibiting the growth and causing differentiation of undifferentiated cells with antisense oligonucleotides complementary to a region of the IGF-1 receptor are provided. The antisense oligonucleotides of the present invention comprise sequences complementary to regions of IGF-1 receptor RNA. The oligonucleotides comprise a sequence complementary to a region selected from the sequence of IGF-1 receptor. The antisense oligonucleotides include DNA sequences; and antisense RNA oligonucleotides produced from an expression vector. Each of the antisense oligonucleotides of the present invention are complementary to regions of the IGF-1 receptor sequence. The antisense oligodeoxynucleotide of the present invention comprises a sequence complementary to codons −29 to −24 of the signal sequence, for example, SEQ ID NO: 4. The signal sequence of IGF-1 receptor is a 30 amino acid sequence. Contemplated by this definition are fragments of oligos within the 30 amino acid signal sequence. Alternatively, fragments of oligos within SEQ ID NO: 4 are also contemplated. The antisense oligoribonucleotide, SEQ ID NO: 8 produced from an expression vector comprise a sequence complementary to codons 1 to 309 of the IGF-1 receptor, FIG. 7. See Ullrich et al., EMBO J., 1986, 5:2503. Contemplated by this definition are fragments of oligos within the coding sequence for the IGF-1 receptor.

BRIEF DESCRIPTION OF THE FIGURES

FIG. 5A is a schematic representation of cell growth of K10 and C2 cells in 10% serum after 5 days. FIG. 5B is a schematic representation of K10 and C2 cells transfected with T antigen (K10a58 and C2a58 respectively). The K10 cells have not been fully transformed.

FIGS. 7A–7G provide the amino acid and nucleotide sequence of IGF-1 receptor. (SEQ ID. NO:9)

DETAILED DESCRIPTION OF THE INVENTION

Figure 1A:
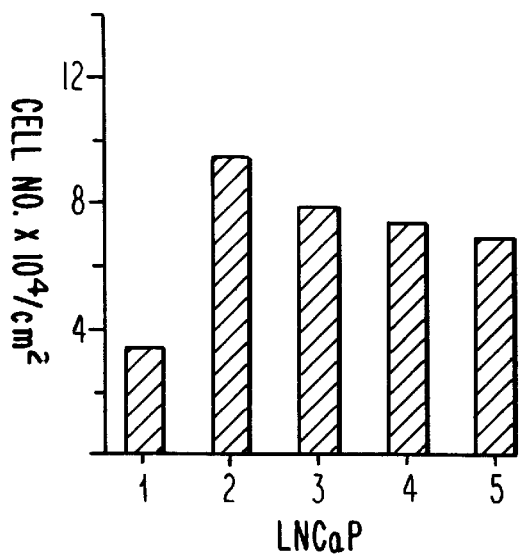
FIGS. 1A, 1B and 1C are schematic representations of the effect of individual growth factors on the growth prostatic cancer cell lines (abscissa). Bars: 1—48 hours after plating; 2—no additions (96 hours after plating); 3—epidermal growth factor (EGF) (20 ng/ml, 96 hours after plating); 4—insulin-like growth factor (IGF-1) (20 ng/ml, 96 hours after plating); 5—platelet derived growth factor (PDGF) (1 ng/ml, 96 hours after plating).

Methods of inhibiting the proliferation of and causing the differentiation of undifferentiated cells are provided by the present invention. In one embodiment, an antisense oligonucleotide having a sequence complementary to codons −29 to −24 of the signal sequence of the IGF-1 receptor was found to be effective.

For purposes of the present invention, undifferentiated cells include and are not limited to transformed cells, cancer cells, prostate cancer cells, ovarian cancer cells, mammary cancer cells, lung cancer cells, glioblastoma cells, smooth muscle cells, bone marrow stem cells, hematopoietic cells, osteoblasts, epithelial cells, fibroblasts. Abnormal cells are cells which do not grow in accordance with the predicted patterns of a selected cell type, including and not limited to cancer cells such as those identified above, and transformed cells.

For purposes of the current invention, mammals include, but are not limited to the Order Rodentia, such as mice;

Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

Figure 7D:
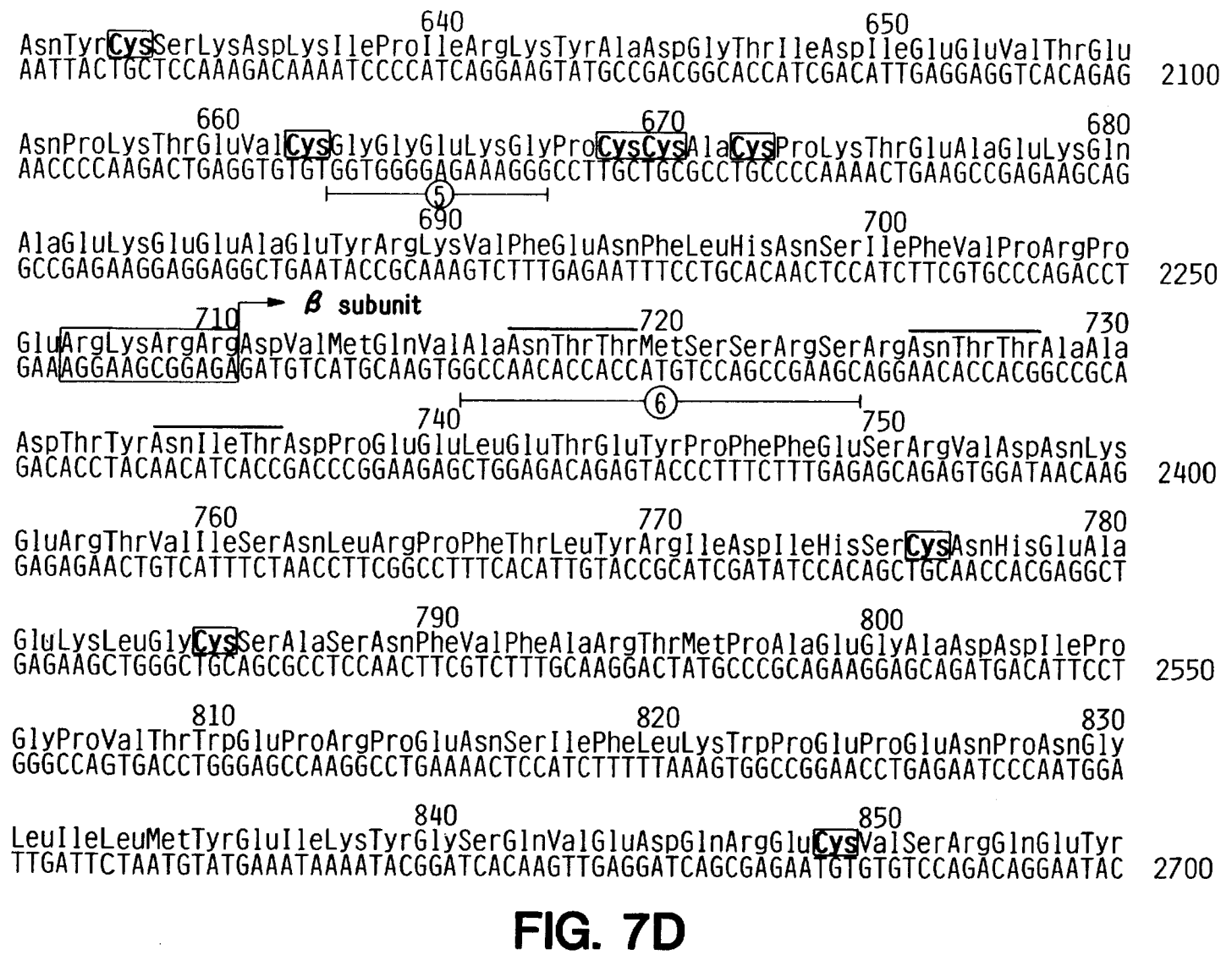

The antisense oligonucleotides of the present invention comprise sequences complementary to regions of IGF-1 receptor RNA. The oligonucleotides comprise a sequence complementary to a region selected from the sequence of IGF-1 receptor. The antisense oligonucleotides include single stranded DNA sequence and an antisense RNA oligonucleotide produced from an expression vector. Each of the antisense oligonucleotides of the present invention are complementary to regions of the IGF-1 receptor sequence. The antisense oligodeoxynucleotide of the present invention comprises a sequence complementary to codons −29 to −24 to the signal sequence, for example, SEQ ID NO: 4. The signal sequence of IGF-1 receptor is a 30 amino acid sequence. Contemplated by this definition are fragments of oligos within the 30 amino acid signal sequence. Alternatively, fragments of oligos within SEQ ID NO: 4 are also contemplated. The antisense oligoribonucleotide, SEQ ID NO: 8 produced from an expression vector comprises a sequence complementary to codons 1 to 309 of the IGF-1 receptor, FIG. 7. See Ullrich et al., *EMBO J.*, 1986, 5:2503. Contemplated by this definition are fragments of oligos within the coding sequence for the IGF-1 receptor. In addition, mismatches within the sequence identified above, which achieve the methods of the invention, such that the mismatched sequences are substantially complementary to the IGF-1 sequences identified above, are also considered within the scope of the disclosure. Mismatches which permit substantial complementarity to the IGF-1 sequences will be known to those of skill in the art once armed with the present disclosure. The oligos may also be unmodified or modified.

The present invention is also directed to a method of treating mammals having cancer comprising contacting the mammal with an effective amount of an antisense oligonucleotide having a sequence which is complementary to a region of the IGF-1 receptor RNA. Cancer cells contemplated by the present invention include and not limited to those identified above.

Methods of administering the antisense oligos of the present invention include techniques well known in the art such as and not limited to liposomes, plasmid expression, retroviral vectors, splicing an oligo to another sequence such as a promoter or a growth factor, wherein the plasmid and/or vector is transfected with an expression plasmid expressing the antisense oligonucleotide, exposing cells to a medium or wash containing the oligo. In the administration of oligos via vectors or plasmids, a non-coding RNA strand of IGF-1 receptor is preferably used in order to produce antisense RNA oligos which are expressed by the cell. The RNA oligos then bind IGF-1 sense or coding RNA sequence. Accordingly, an oligo RNA sequence similar to SEQ ID NO: 4 is used. In the administration of a medium or wash, antisense DNA is preferably used. an oligo DNA, similar to SEQ ID NO: 4, and SEQ ID NO: 7

Methods of administering the oligos to mammals include liposomes, and may be in a mixture with a pharmaceutically-acceptable carrier, selected with regard to the intended route of administration and the standard pharmaceutical practice. In addition, antibodies, ligands and the like may be incorporated into the liposomes thereby providing various modes of inhibiting IGF-1 receptors at the same time. Dosages will be set with regard to weight, and clinical condition of the patient. The proportional ratio of active ingredient to carrier will naturally depend on the chemical nature, solubility, and stability of the compounds, as well as the dosage contemplated. The oligos of the present invention will be administered for a time sufficient for the mammals to be free of undifferentiated cells and/or cells having an abnormal phenotype.

The oligos of the invention may be employed in the method of the invention singly or in combination with other compounds. The amount to be administered will also depend on such factors as the age, weight, and clinical condition of the patient. See Gennaro, Alfonso, ed., Remington's Pharmaceutical Sciences, 18th Edition, 1990, Mack Publishing Co., Easton Pa.

The compounds of the present invention may be administered by any suitable route, including inoculation and injection, for example, intravenous, oral, intraperitoneal, intramuscular, subcutaneous, topically, and by absorption through epithelial or mucocutaneous linings, for example, nasal, oral, vaginal, rectal and gastrointestinal.

The mode of administration of the oligos may determine the sites in the organism to which the compound will be delivered. For instance, topical application may be administered in creams, ointments, gels, oils, emulsions, pastes, lotions, and the like. The oligos of the present invention may be administered alone or will generally be administered in admixture with a pharmaceutical carrier selected with regard to the intended route of administration and standard pharmaceutical practice. For parenteral administration, they are best used in the form of sterile aqueous solution which may contain other solutes, for example, sufficient salts, glucose or dextrose to make the solution isotonic. For oral mode of administration, the present invention may be used in the form of tablets, capsules, lozenges, troches, powders, syrups, elixirs, aqueous solutions and suspension, and the like. Various disintegrants such as starch, and lubricating agents may be used. For oral administration in capsule form, useful diluents are lactose and high molecular weight polyethylene glycols. When aqueous suspensions are required for oral use, certain sweetening and/or flavoring agents may be added. Forty $\mu$g/ml antisense oligo was used for in vitro methods of providing oligos in media for cell growth in culture. This concentration may be extrapolated for in vivo use. The concentration of antisense oligodeoxynucleotides for in vivo use is about 40 $\mu$/g body weight. The in vivo use of the expression vector expressing RNA oligonucleotides is determined by the number of transfected cells.

The growth of prostatic cancer cell lines was inhibited by antisense oligonucleotides to IGF-1 receptor RNA indicating that these cells need a functionally activated IGF-1 receptor for growth. These compositions are nontoxic at the concentrations used and are very effective and easy to deliver. These compositions may be useful in the treatment of prostatic cancer and other forms of abnormal growth because IGF-1 is a required growth factor for a wide variety of cell types and its action seems to be located downstream from other growth factors receptors. Therefore, while cells could circumvent other growth factor requirements by establishing and IGF-1/IGF-1 receptor autocrine loop, for many cell types, the activation of the IGF-1 receptor is the last receptor-mediated event before DNA synthesis and mitosis, and, presumably cannot be circumvented except by intracellular substrates of the IGF-1 receptor. Methods of reversing the transformed phenotype of cells with abnormal growth potential are also provided.

Figure 1B:
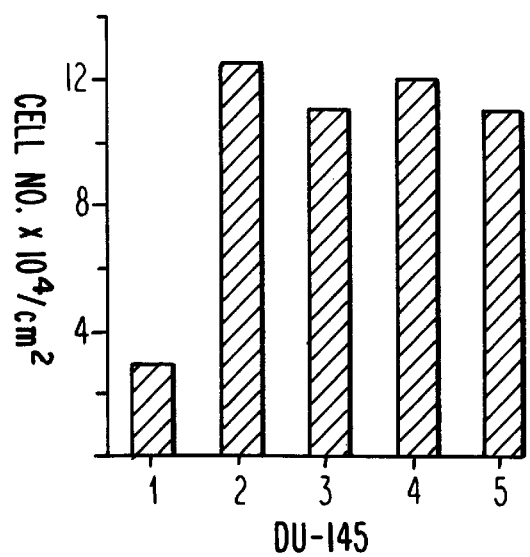
Figure 1C:
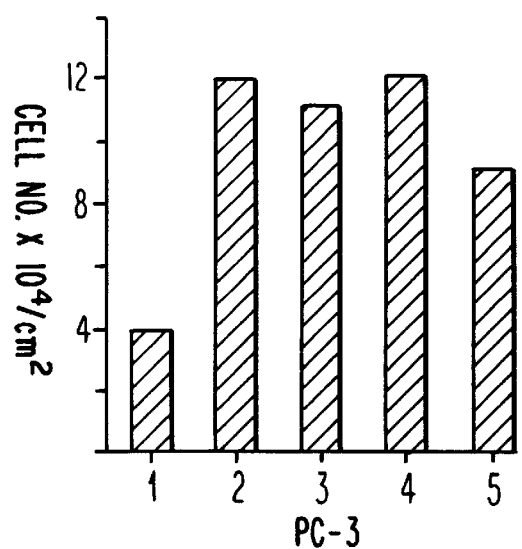
Figure 2:
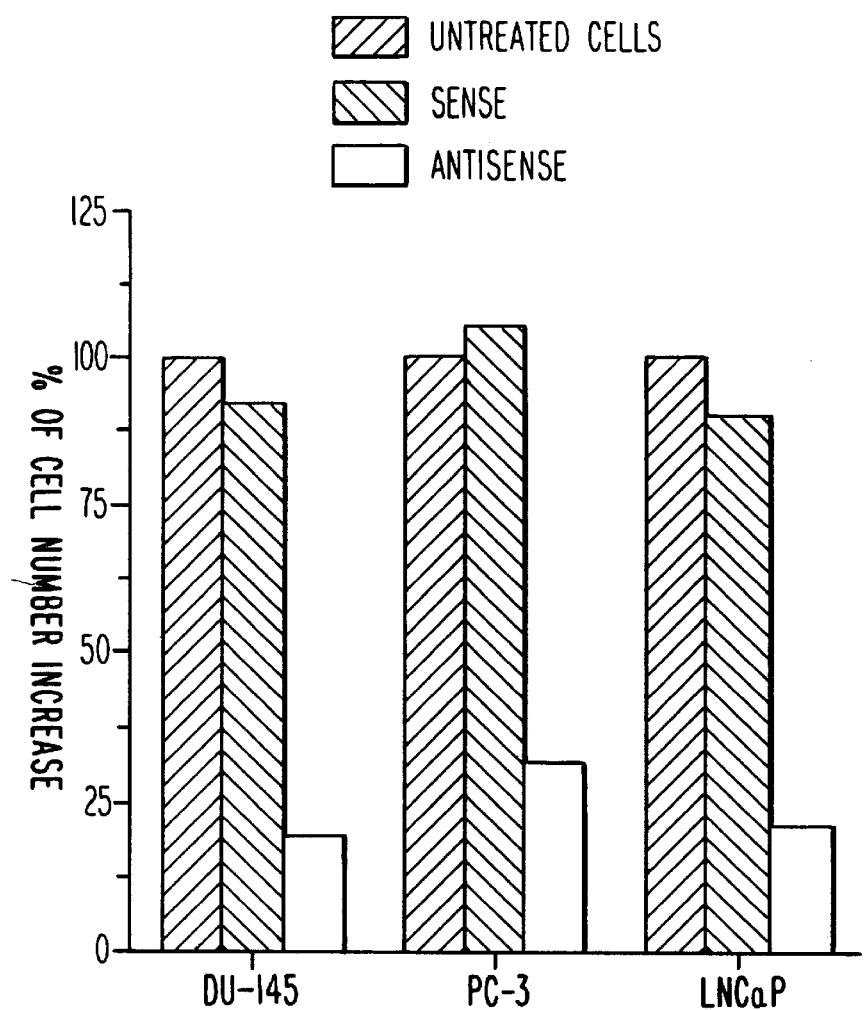
FIG. 2 is a schematic representation of the effect of antisense oligonucleotide to the IGF-1 receptor on the growth of prostatic cancer cell lines. Bars 1, 4, and 7 (control). Bars 2, 5, and 8 (sense). Bars 3, 6, and 9 (antisense).

In one series of experiments, well established cell lines that were adapted to grow in vitro and that originated from sources of human prostatic cancer are examined. The effect of individual growth factors on the growth of these prostatic cancer cell lines is shown in FIG. 1. The effect of an antisense oligodeoxynucleotide to the IGF-1 receptor RNA on the growth of these cells lines is shown in FIG. 2. The effects of antisense oligodeoxynucleotide to the IGF-1 receptor RNA on the growth of Balb 58 cells, human glioblastoma cells, human ovarian cancer cells, and HL-60 cells are also shown. As the data show, these cells need a functionally activated IGF-1 receptor for growth. Any cells having an IGF-1 receptor may be targeted by methods of the present invention. For example, leukemic cells, cancer cells, and smooth muscle cells may be targeted by methods of the present invention. The potential usefulness of such an antisense composition in the treatment of prostatic cancer and other forms of abnormal growth is shown by the observation that IGF-1 is a required growth factor. In other words, while the cells could circumvent other growth factor requirements by establishing an IGF-1/IGF-1 R autocrine loop, the activation of the IGF-1 receptor (IGF-1 R) is the last receptor-mediated event before DNA synthesis and mitosis, and presumably, cannot be circumvented except by intracellular substrates of the IGF-1 receptor. The experiments show that the IGF-1/IGF-1 receptor pathway plays an important role in the growth and differentiation of cancer cell lines and that antisense composition can inhibit their growth and cause differentiation.

Furthermore, methods of reversing transformed phenotype of cells with abnormal growth potential are provided by the present invention. For example, since the absence of IGF-1 receptor has been found to decrease cell growth by 70%, but completely inhibits the transformed phenotype, this approach can differentially affect cells having an abnormal phenotype, such as cancer cells, by reversing the transformed phenotype at concentrations of antisense that only partially affect normal growth. Reversal of the transformed phenotype causes differentiation that is usually irreversible. Furthermore, the cells may become immunogenic towards themselves providing an additional benefit.

For in vivo use, the antisense oligonucleotide may be combined with a pharmaceutically acceptable carrier, such as suitable liquid vehicle or excipient and an optional auxiliary additive or additives. The liquid vehicles and excipients are conventional and commercially available. Illustrative thereof are distilled water, physiological saline, aqueous solution of dextrose, and the like. For in vivo antineoplastic use, the antisense oligonucleotides may be administered intravenously.

In addition to administration with conventional carriers, antisense oligonucleotides may be administered by a variety of specialized oligonucleotide delivery techniques. For example, oligonucleotides have been successfully encapsulated in unilamellar liposomes. Reconstituted Sendai virus envelopes have been successfully used to deliver RNA and DNA to cells. Arad et al., *Biochem. Biophy. Acta.*, 1986, 859, 88–94.

The invention is further illustrated by the following, non-limiting examples.

EXAMPLES

EXPERIMENT A

Example

Cell Lines

The following cells lines were used.
1) Balb/c 3T3 cells;
2) mouse embryo cells established as primary cultures from normal mouse embryo;
3) KO cells, established from littermate embryos, null for the IGF-1 receptor;
4) three human prostatic cancer cell lines obtained from the American Tissue Culture Collection: PC-3 (originating from a human adenocarcinoma of the prostate; ATCC# HTB81); LNCa.FGC ("LNC"; from a human metastatic adenocarcinoma of the prostate, ATCC# CRL1740); and DU-145 (from a human carcinoma of the prostate metastatic to the brain, ATCC# CRL1435);
5) a human ovarian carcinoma cell line, ON-CAR; ATCC# HTB161
6) Balb 58 cells, Porcu et al., *Mol. Cell. Biol.* 1992, 12, 5069–5077;
7) T98G cells, a glioblastoma cell line originating from a human glioblastoma; and
8) HL-60 cells, a well established human promyelocytic cell line.

Human prostatic cell lines were passaged as recommended by the ATCC; they are grown in the following serum free media: DU-145 in MEM supplemented with 1 $\mu$M ferrous sulfate, 1 mM sodium pyruvate and 0.1% bovine serum albumin (BSA). The same supplements were added to DMAM:RPMI 1640 (1:1) to grow PC-3 cells, and to RPMI 1640 for LNC cells.

Example 2

Growth in Serum-Free Medium

The cells were plated first in 10% calf serum in order to provide attachment factor. Alternatively, poly-L-lysine may be used. Pietrzkowski et al., *Mol. Cell. Biol.* 1992, 12, 3883–3889. The growth medium was removed by careful and repeated washing after twenty four hours and replaced with serum-free medium, with the sole additions of bovine serum albumin (0.5 mg/ml) and ferrous sulfate, 1.0 $\mu$M. The number of cells was determined by standard methods at the times indicated in each individual experiment. All three cell lines, DU-145, PC-3, and LNC grow in serum-free medium as vigorously as in serum supplemented medium, unlike 3T3, p6 and human diploid fibroblasts which do not grow under serum-free conditions. Pietrzkowski et al., *Mol. Cell. Biol.* 1992, 12, 3883–3889.

Example 3

Effect of Growth Factors on Prostatic Cancer Cell Lines

Cells were cultured as described in Example 2. Epidermal growth factor (EGF) (20 ng/ml), platelet derived growth factor (PDGF) (1 ng/ml) or insulin-like growth factor-1 (IGF-1) (20 ng/ml) were added to individual cell cultures. No increase in cell growth was observed 96 hours after plating of DU-145 and PC-3 cell lines. The growth factors showed slight inhibitory effect on LNC cells 96 hours after plating.

Example 4

Reverse-Transcriptase Polymerase Chain Reaction (RT-PCR)

The prostatic cancer cell lines were tested for their ability to express IGF-1 receptor RNA by RT-PCR after incubation of cells in serum-free medium for 48 hours. Reverse-transcriptase polymerase chain reaction was performed by slight modification of the method of Rappolee et al., *J. Cell. Biochem.* 1989, 39, 1–11; Lipson et al., *Proc. Natl. Acad. Sci. U.S.A.* 1989, 86, 9774–9777. RNA was extracted from cells by slight modification of the method of Chomczynski and Sacchi, *Anal. Biochem.* 1987, 162, 156–159. Amplimers and probe for the IGF-1 receptor RNA were chosen on the basis of the published cDNA sequence of the human IGF-1 receptor. Ullrich et al., *EMBO J.* 1986, 5, 2503–2512, 5' amplimer, 5' ACC ATT GAT TCT GTT ACT TC 3' (SEQ ID NO: 1); 3' amplimer, 5' ATA CTC TGT GAC ATT CTT AA 3' (SEQ ID NO: 2); probe, 5' CTG CTC CTC TCC TAG GAT GA 3' (SEQ ID NO: 3). Labeling of probes and hybridization were carried out by standard methods as described for example by Feinberg and Vogelstein, *Anal. Biochem.* 1983, 132, 6–13 and Thomas, P. S., *Methods Enzymol.* 1983, 100, 255–266. The various controls used in the RT-PCR assays (elimination of DNA, rejection of samples that give signals without reverse transcriptase, and multiple amplification cycles) are described for example by Pietrzkowski et al., *Cell Growth & Diff.* 1992, 3, 199–205; Pietrzkowski et al., *Mol. Cell. Biol.* 1992, 12, 3883–3889; Reiss et al., *Oncogene* 1992, 7, 2243–2248. RNA amounts were monitored with amplimers and probe for the pHE 7 cDNA, ribosomal protein cDNA, whose cognate RNA is expressed constantly under different conditions of growth. Reiss et al., *Oncogene* 1992, 7, 2243–2248.

Figure 3:
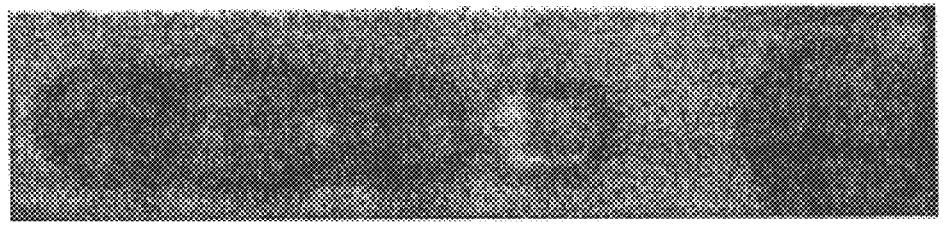
FIG. 3 is an autoradiogram of RT-PCR to determine the level of IGF-1 RNA produced by 5 different cell lines. Lane 1: PC-3; Lane 2: DU-145; Lane 3: LNC cells; Lane 4: WI-38 human diploid fibroblasts; Lane 5: p12 cells.

Results are shown in FIG. 3. RNAs from PC-3 cells (lane 1), DU-145 cells (lane 2), LNC cells (lane 3), WI-38 human diploid fibroblasts (lane 4, normal control) and p12 cells (which constitutively overexpress IGF-1 receptor RNA; lane 5) are shown. WI-38 cells and p12 cells were included as examples of cells which require IGF-1 for growth. Chomczynski, and Sacchi, *Anal. Biochem.* 1987, 162, 156–159.

Two of the cell lines, PC-3 and CU-145 express levels of IGF-1 receptor RNA that are about 10-fold (by densitometry) the levels in WI-38 cells. LNC cells express levels that are only slightly above those of WI-38. The amounts of RNA in each reaction were within 10% of each other.

Example 5

Antisense Experiments

Antisense and sense oligonucleotides corresponding to portions of codon −29 to −24 of the signal sequence of the human IGF-1 receptor preceding the proreceptor sequence, Ullrich et al., *EMBO J.* 1986, 5, 2503–2512 were prepared. The oligodeoxynucleotides were synthesized on an Applied Biosystem Model 391 EP DNA synthesizer using β-cyanoethyl phosphoramidite chemistry. Pietrzkowski et al., *Cell Growth & Diff.* 1992, 3, 199–205; Pietrzkowski et al., *Mol. Cell. Biol.* 1992, 12, 3883–3889; Reiss et al., *Oncogene* 1992, 7, 2243–2248.

Phosphorothioate oligonucleotides having sequences corresponding to codons −29 to −24 of the signal sequence, having the sequences TCCTCCGGAGCCAGACTT (SEQ ID NO: 4; antisense) and GCACCGGGAAGTTGTGTCAA (SEQ ID NO: 6; mismatched) were prepared as described above. 40 µg/ml of the oligonucleotides were added to SV-40 transformed Balb 58 cells (L clone; Porcu et al., *Mol. Cell. Biol.* 1992, 5069–5077), in 1% serum at 34° C. The cells were counted after 72 hours. The antisense oligonucleotide caused an 85% inhibition of cell growth as compared to a control (no addition of oligonucleotide). The mismatched antisense oligonucleotide resulted in only a 15% inhibition of cell growth.

Three human prostatic cancer cell lines were also treated with antisense phosphorothioate oligonucleotides. The oligonucleotides had the sequences TCCTCCGGAGCCA-GACTT (SEQ ID NO: 4; antisense) and AAGTCTGGCTC-CGGAGGA (SEQ ID NO: 5; sense). Pietrzkowski et al., *Cell Growth & Diff.* 1992, 3, 199–205. The oligodeoxynucleotides were added to the medium after 48 hours in serum-free medium (40 µg/ml) and the treatment was repeated the next day (20 µg/ml). The cells were counted 48 hours after the second addition. FIG. 2 shows that antisense oligonucleotides to IGF-1 receptor RNA markedly inhibited all three prostatic cancer cell lines, the inhibition varying from 70 to 90%. After 48 hours treatment, the prostatic cancer cells look flat, polygonal, with the characteristics of a normal epithelial cell.

Antisense studies were also carried out on an ovarian carcinoma cell line and on a glioblastoma cell line. The results are summarized in TABLE 1.

TABLE 1

Effect of Antisense Oligodeoxynucleotides to the
IGF-1 Receptor RNA on the Growth of Human Cancer Cell Lines

| cell lines | Inhibition of growth % | |
|---|---|---|
| | antisense | sense |
| T98G (human glioblastoma) | 90 | 12 |
| ON-CAR (human ov. ca.) | 100 | 2 |

Cells were grown in serum-free medium supplemented with individual growth factors and the antisense or sense phosphorothioate oligonucleotides at concentrations of 40 µg/ml. The oligonucleotides had the sequences TCCTCCG-GAGCCAGACTT (SEQ ID NO: 4; antisense) and AAGTCTGGCTCCGGAGGA (SEQ ID NO: 5; sense). The inhibition is based on the growth of control cells (no oligos added). Cells treated with antisense showed signs of differentiation, with flattening, contact inhibition and reversal of the transformed phenotype.

HL-60 cells were also treated with the antisense phosphorothioate oligonucleotides. The oligonucleotides had the sequences TCCTCCGGAGCCAGACTT (SEQ ID NO: 4, antisense) and AAGTCTGGCTCCGGAGGA (SEQ ID NO: 5; sense). When HL-60 cells were treated with antisense oligonucleotides to the IGF-1 receptor RNA, the cells differentiated toward a macrophage lineage, just as when they are treated with a differentiating agent.

Example 6

Autophosphorylation of the IGF-1 Receptor

Figure 4:
FIG. 4 is a western blot showing autophosphorylation of IGF-1 receptor. Lane 1: p12 cells 48 hours in serum-free medium, Lanes 2–4: PC-3, DU-145, and LNC cells respectively, 48 hours in serum-free medium 15 minutes after the addition of IGF-1 (3 ng/ml), Lanes 5–7: PC-3, DU-145 and LNC cells respectively, 48 hours in serum-free medium, no added IGF-1.

The cells were characterized for levels of IGF-1 receptor that can be autophosphorylated by IGF-1. Autophosphorylation was carried out by slight modification of the method of Lammers et al., *EMBO J.* 1989, 8, 1369–1375, using the monoclonal antibody to the IGF-1 receptor available from Oncogene Sciences (Uniondale, N.Y.), an anti-phosphotyrosine antibody available from UBAI (Saranac Lake, N.Y.), and the ECL detection system kit from Amersham (Arlington Heights, Ill.). Protein lysates were obtained from cells growing for 48 hours in serum free medium. Before lysis, the cells were treated for 2 hours with sodium orthovanadate (1 mM). Results are shown in FIG. 4.

Although the amount of autophosphorylated IGF-1 receptor is not as high as in p12 cells (lane 1), which constitutively overexpress the human IGF-1 receptor, substantial amounts of receptor that can be autophosphorylated by IGF-1 are detectable in all cell lines (lanes 2–4). More significantly, the autophosphorylation of the receptor can be detected in cells growing in serum-free medium even without the addition of IGF-1 (lanes 5–7), indicating that, in these cell lines, the IGF-1 receptor is constitutively autophosphorylated due to the presence of measurable amounts of IGF-1 secreted by the cells themselves into the medium.

Example 7

IGF-1 Radioimmune Assay

The ability for the cells to produce and secrete IGF-1 in the medium was determined by radioimmune assay. The radioimmune assay was performed essentially as described by Pietrzkowski et al., *Mol. Cell. Biol.* 1992, 12, 3883–3889. Cells were incubated in serum-free medium for 72 hours. Conditioned medium containing 1% bovine serum albumin (BSA) and 1 mM ferric sulfite was collected at various times after the cells were transferred to serum-free medium. To remove IGF-1 binding proteins, 0.1 ml of conditioned medium was mixed with 900 ml of 1 M acetic acid and 5% BSA and loaded onto SepPak C18 columns (Waters, Milford, Mass.). Before loading, the column was washed with 10 ml of methanol and then by 10 ml $H_2O$. After loading, the column was washed with 10 ml of 4% acetic acid, and IGF-1 was eluted in 1 ml of 50% acetonitrile and 4% acetic acid. After lyophilization, the sample was resuspended directly in 100 ml of radioimmunoassay buffer. The assay was performed with a rabbit IGF-1 anti-serum and a second antibody bound to magnetic beads (Amersham, Arlington Heights, Ill.) using a commercially available radioimmunoassay kit (Amersham, Arlington Heights, Ill.) The results are shown in TABLE 2.

TABLE 2

| Cell Line | Amount of IGF-1 in ng IGF-1/ml/2 × $10^6$ cells |
|---|---|
| DU-145 | 12.06 |
| LNC | 14.38 |
| PC-3 | 24.36 |

As seen in TABLE 2, all three cell lines are good producers of IGF-1, especially PC-3. In all instances, however, the concentration of IGF-1 is more than sufficient to autophosphorylate the IGF-1 receptor and to sustain growth if the number of IGF-1 receptors is adequate.

For example, ordinarily, in cells expressing an adequate number of IGF-1 receptors, like p6 cells, 3.0 ng/ml of IGF-1 are sufficient to induce autophosphorylation of the receptor and stimulation of growth.

Example 8

SV40 T Antigen

For transformation, pts58H, a plasmid which contains the tsA58 T antigen coding gene, cloned in pBR322, was used as well as the hygromycin resistance hph cDNA under the control of a viral promoter. Porcu et al., *Mol. Cell. Biol.,* 1992, 12, 5069–507. Clones of cells transfected with this construct are selected in hygromycin.

KO cells (no IGF-1 receptors) grow in 10% serum at a rate that is roughly 40% the rate of wild type cells (MEC cells). IAs shown in FIG. 5, panel A, these cells are indicated as K10 and C2 cells. Both MEC and KO cells were transfected with the plasmid tsA58H, carrying the SV40 T antigen and a selectable marker. Clones were selected in hygromycin; because of the plasmid used, all cells in all clones were 100% T antigen positive.

FIG. 5, Panel B, shows the growth characteristics of these two types of cells, transfected with T antigen, and which we call KI 0a58 and C2a58. The figure gives the saturation density of these two cell lines. The saturation density of C2a58 cells is 4-fold the saturation density of KI 10a58. The latter one formed a contact-inhibited monolayer, while C2a58 cells were forming foci, like transformed cells. This suggests that T antigen has not been able to fully transform the KO cells.

Example 9

Soft agar assay was carried out by standard methods. A more convincing way to test for transformation is to grow cells in soft agar, a test that has been used for many years to characterize transformed cells. Untransformed cells do not form colonies in soft agar; only transformed cells can form colonies, and the number of colonies formed is usually taken as an index of transformation. Cells were tested in soft agar, and the results of such an experiment are shown in TABLE 3.

TABLE 3

Growth in Soft Agar of Various Cell Lines

| cell lines | number of colonies formed |
|---|---|
| Balb/c 3T3 cells | 0 |
| Balb58 cells (transformed 3T3) | >200 |
| T98G (human glioblastoma) | >100 |
| MEC cells | 0 |
| KO cells | 0 |
| T-MEC cells (T transformed) | >200 |
| T-KO cells (T-transfected) | 0 |

One thousand cells of each cell line were seeded and the number of colonies determined after 2 weeks.

The prostatic cancer cell lines and the ovarian carcinoma cell line also grow in soft agar, as reported by other investigators. TABLE 3 clearly show that a strong oncogene like SV40 T antigen is incapable of transforming cells that do not have IGF-1 receptors. Experiments are in progress in nude mice: preliminary data indicate, as anticipated, that T-KO cells do not grow in nude mice, whereas other T-transformed mouse cells do.

EXPERIMENT B

Example 10

Cell Cultures and Plasmid Construction

Mouse embryos were dissected from anesthetized females at day 18 of gestation and genotyped using DNA prepared from the mouse tails by Southern analysis as described by Liu, et al., *Cell,* 1993, 75:59 and Baker et al., *Cell,* 1993, 75:73. Wild-type and homozygous IGF-1 receptor mutant (Igf1r (-1-)) littermates were used for establishing primary cultures of embryonic fibroblasts as described by Warton, et al., in *Cell Growth and Division,* 1989, 139–153, Baserga, ed, IRL Press, Oxford, England.

The embryos were minced, and treated with trypsin for 15 minutes. The cells of the resulting suspension were plated onto 100 mm culture dishes and cultured in Dulbecco's modified Eagle's medium (DMEM: GIBCO-BRL, Grand Island, N.Y.) supplemented with 10% fetal bovine serum. The cultures were maintained at subconfluent levels by trypsinizing every three days and reseeding at a density of $1.5 \times 10^3$ cells/cm$^2$, following the same protocol used to generate 3T3 cell lines. Todaro, et al., *J. Cell Biol.*, 1963, 17, 299. Primary cultures underwent crisis following 2–4 weeks in culture. Crisis results in immortalized cells. Cells null for IGF-1 receptor, R-, cultures entered crisis later than the wild-type cells due to the relatively slow doubling rate.

Cells from wild-type and homozygous Igf1r (-1-) mutant embryos were established initially as primary cultures and subsequently as post-crisis cell lines, which will be referred to an parental lines W and R-, respectively. These lines, which were derived by a protocol previously used to generate 3T3 cells, have a fibroblast-like appearance. Todaro, G. J. et al., *J. Cell Biol.*, 1963, 17:299. In serum-free medium supplemented with PDGF (5 ng/ml), EGF (20 ng/ml) and IGF-1 (20 ng/ml), W cells grow well, while R- cells fail to increase in number. Growth of R- cells can be sustained in 10% serum, but their growth rate is only 40–50% that of W cell controls (see TABLE 4). The growth of W cells under the conditions of TABLE 4 is essentially the same as that of the Balb/c 3T3 cells.

TABLE 4

GROWTH OF W AND R- CELLS IN CULTURE

| CELL TYPE | GROWTH FACTORS | NUMBER OF DOUBLINGS |
|---|---|---|
| W Cells | PDGF, EGF, IGF-1 | 1.5 |
| W Cells | 10% serum | 3.0 |
| W Cells | serum-free medium | 0 |
| R- Cells | PDGF, EGF, IGF-1 | 0 |
| R- Cells | 10% serum | 1.5 |
| R- Cells | Serum-free medium | 0 |

Cells were seeded at a concentration of $5 \times 10^3$, cells/cm$^-$ in plastic dishes, in DMEM supplemented with 10% fetal calf serum. After 24 hours, the growth medium was removed, the cells washed several times with Hanks' solution and DMEM was added with the indicated supplements. Cells were counted at 48 and 72 hours after changing to the indicated condition. The number of doublings shown represents 72 hours.

Indirect biochemical analysis showed that a functional IGF-1R is absent from primary cultures of cells isolated from day 14.5 Igf1r (-1-) mutant embryos. Liu, et al., *Cell*, 1993, 75:59 and Baker et al., *Cell*, 1993, 75:73. To confirm this result using a specific antibody and establish unequivocally that R- cells are completely devoid of IGF-1 receptor, the following experiment was performed.

After incubation in the presence of IGF-1 for ligand-activated autophosphorylation of the IGF-1 receptor, R- cells and control W cells were lysed and a polyclonal antibody against the β subunit of mouse IGF-1 receptor was added to immunoprecipitate and functional IGF-1 receptor present in the lysate. The precipitated proteins were solubilized in the presence of β-mercaptoethanol, resolved electrophoretically and transferred to a nitrocellulose membrane. The β subunit of IGF-1 receptor autophosphorylated in an IGF-1-dependent fashion, was visualized by immunostaining with an antiphosphotyrosine antibody (UBL, Saranac Lake, N.Y.) and recognized by size, and by the response to IGF-1. The apparent molecular weights of the α and β subunits of IGF-1 receptor resolved electrophoretically after disulfide bond reduction and denaturation are 135 kD and 97 kD, respectively. Autophosphorylation of β subunit (97 kD species) was detected, after IGF-1 stimulation, in W cells, but not in R- cells.

For confirmation the presence of the α subunit of the IGF-1 receptor was examined by cross-linking radioiodinated IGF-1 to cell membranes, followed by electrophoretic analysis and autoradiography. Yamori, et al., *Cancer Res.*, 1991, 51, 5859. A labeled protein of 135 kD was easily detectable in W cells, and its signal could be eliminated by competing the radioiodinated ligand with a 1,000 fold excess of unlabeled IGF-1. In contrast, it was not possible to detect a labeled protein species of this size in R- cells, even after significant overexposure of the autoradiogram.

Figure 6:
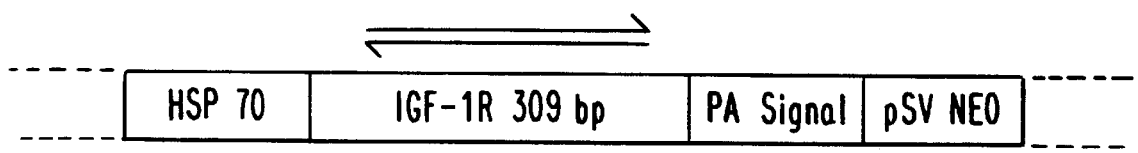
FIG. 6 is a diagram of the plasmid constructs IGF-1RS and IGF-1RAS.

T98G cells are a human glioblastoma cell line, that produces large amounts of IGF-1. Stein, G. H., *J. Cell. Physiol.*, 1979, 99:43. Two other cell lines were generated from T98G cells, expressing, respectively, a sense and an antisense RNA to the human IGF-1 receptor RNA. Expression plasmids which generate mRNA sequences, sense or antisense to the human IGF-1 receptor, were constructed. The human heat shock promoter HSP 70 was excised from the pSp2 (Craig et al., *Cell*, 1979, 16:575) with PstI and inserted into the SalI site of the pUC 18 multiple cloning site (MCS). The hepatitis B polyadenylation (PA) signal sequence and a neomycin resistance gene under control of the simian virus 40 (SV40) promoter were cloned into the BamHI site of the multi-cloning site to generate the plasmid HSP-neo. An XbaI-XhoI fragment corresponding to the bp 1–309 of the IGF-1 receptor cDNA (Ullrich et al., *EMBO J.* 1986, 5, 2503–2512) was filled-in with Klenow, and blunt end ligated into a filled-in BamHI site of the plasmid HSP-neo. The resulting plasmids were restricted and sequenced to determine the orientation of the transcripts. The plasmids predicted to produce the sense and antisense transcripts of the IGF-1 receptor cDNA were named HSP-IGF-1RS and HSP-IGF-1RAS, respectively, see FIG. 6. Transfections were performed using the calcium phosphate precipitation method (Shen et al., *Mol. Cell. Biol.*, 1982, 2:1145). After 48 hours, 1 mg/ml neomycin was added to the cells to obtain stable transfectants.

Cells were seeded at a density of $3 \times 10^3/35$ mm plate in 10% serum on a top layer of 0.3% agar and a bottom support layer of 1% agar. Colonies of greater than 10 cells were counted 14–21 days later.

C6 cells are a rat glioblastoma cell line. Trojan et al., *PNAS*, 1992, 89:4874 and Trojan et al., *Science*, 1993, 259:94.

Example 11

Plasmid Transfection

Cells were transfected with DNA of the following plasmid constructs: a) ptsA58H (Porcu, et al., *Mol. Cell. Biol.*, 1992, 12:5069) which contains the hygromycin-resistance gene (hyg) and the sequence encoding tsA58, a temperature-sensitive SVLT (Tegtmeyer, *J. Virol.*, 1975, 15:613); b) pSV2G (Floros, et al., *Exp. Cell Res.*, 1981, 132:215), which contains the sequence encoding the wild-type SV40 T antigen and which was co-transfected with a plasmid containing the hygromycin resistance gene (LHL4) (Gritz, et al., *Gene*, 1983, 25:179); and c) Cvn-IGF-1 receptor, which contains the neomycin resistance gene (neo) and the entire coding sequence of the human IGF-1 receptor cDNA, both of which are under control of the SV40 promoter; as described by Porcu, et al., *Mol. Cell. Biol.*, 1992, 12, 5069.

Primary cultures were extremely sensitive to hygromycin and selection was carried out in 10 μg/ml of hygromycin. Cell proliferation in anchorage-dependent conditions was assayed by trypsinizing the cells and counting in triplicate every 24 hours, using a hemocytometer.

Parental W and R- cells were transfected with DNA of a plasmid construct ptsA58H (Porcu, et al., *Mol. Cell. Biol.*, 1992, 12, 5069), containing a selectable marker, the hygromycin-resistance gene (Gritz et al., *Gene*, 1983, 25:179), and the sequence encoding the temperature-sensitive SV40T antigen tsA58 (Tegtmeyer, *J. Virol.,* 1975, 15:613). Cells expressing tsA58 are transformed at the permissive temperature of 34 C, but revert to the untransformed phenotype at the restrictive temperature of 39.6 C (Porcu et al., supra, Lammers, et al., *EMBO J,* 1989, 8:1369, Jat, et al., *Mol. Cell. Biol.,* 1989, 9:1672, Radna et al., *Molc. Cell. Biol.,* 1989, 9:3093, and Resnick-Silverman et al., *J. Virol.,* 1991, 65:2845). Since the selectable marker and T antigen are expressed from the same plasmid, all of the hygromycin-resistant clones derived were also T-positive. Thus, when selected W and R- cells harboring ptsA58H were examined by immunofluorescence using an antibody against T antigen, both cell types exhibited approximately the same level of intensity in staining (45±0.9 and 43.7±0.7 arbitrary densitometric units respectively). These transfected derivatives of the parental W and R- lines were designated (tsA)W and (tsA)R- cells.

The four types of cells [W, R-, (tsA)W and (tsA)R-] were plated and grown in DMEM supplemented with 10% serum for 5 days, and then cell numbers were determined to assess saturation densities. As expected from previous results, the ratio of R- to W cell numbers was 0.53. However, growth was differentially stimulated by the presence of SVLT. The number of (tsA)W cells was 2.7 fold higher than that of W cells, while (tsA)R- cells grew only 30% above the saturation density of the R- parent. More importantly, the (tsA)W cells were overtly transformed, as evidenced by the appearance of large foci, while the (tsA)R- cells continued to be contact-inhibited. Identical results were obtained with several different T positive clones derived from the parental cell lines.

To further assess the presence or absence of a transformed phenotype, we used soft-agar assays (Thompson, et al., *Virology,* 1990, 178:15). The results of a typical experiment are shown in TABLE 5. As expected, (tsA)W cells formed colonies in soft agar in numbers increasing with the number of cells that were seeded, while only a single small colony of 12 cells appeared with the highest number of plated (tsA)R- cells. The cells were maintained in 10% serum for more than 3 weeks, which is a more than adequate time period for establishment of colonies in soft agar even at reduced growth rates. Therefore, the (tsA)R- cells do not have potential for colony formation in soft agar.

TABLE 5

GROWTH IN SOFT AGAR OF MOUSE EMBRYO CELLS EXPRESSING SVLT

| CELL TYPE | SEEDING DENSITY x $10^3$ | NUMBER OF COLONIES |
| --- | --- | --- |
| (tsA) W | 1 | 8 |
| (tsA) W | 10 | 64 |
| (tsA) W | 100 | 350 |
| (tsA) R- | 1 | 0 |
| (tsA) R- | 10 | 0 |
| (tsA) R- | 100 | 1 |
| (wtT) W | 10 | 58 |
| (wtT) W | 100 | 154 |
| (wtT) R- | 10 | 0 |
| (wtT) R- | 100 | 0 |
| (tsA) R+ | 10 | 16 |
| (tsA) R+ | 100 | 70 |

(tsA) W and (tsA) R- are, respectively, W and R- cells expressing the tsA58 T antigen. The same embryo cells expressing the wt T antigen are designated (wtT). (tsA) R+ cells are (tsA) R- cells expressing a stably transfected human IGF-1 receptor cDNA. Parental cell lines, W and R- did not grow in soft agar. Cells were seeded at the indicated densities and colonies were counted after 25 days in culture. Numbers are averages of TABLE 5-continued

GROWTH IN SOFT AGAR OF MOUSE EMBRYO CELLS EXPRESSING SVLT

| CELL TYPE | SEEDING DENSITY x $10^3$ | NUMBER OF COLONIES |
| --- | --- | --- | duplicate counts of a single experiment. Several assays were performed with reproducible results for each cell line. Several clones of (tsA) and (wtT) cells were also tested with similar results.

To exclude the possibility that the temperature-sensitive T antigen is somehow different from wild-type, additional lines were derived from the parental W and R- cells by co-transfecting two plasmids expressing wild-type SVLT and the hygromycin-resistance gene, respectively. Following hygromycin-selection, cells testing positive for T antigen expression were expanded into clones that were assayed for colony formation in soft agar. Again, in contrast to controls, the derivatives of R- cells were unable to form colonies, TABLE 6.

TABLE 6

GROWTH IN SOFT AGAR OF GLIOBLASTOMA CELL LINES TREATED BY ANTISENSE STRATEGY TO THE IGF-1 RECEPTOR

| CELL TYPE | SEEDING DENSITY x $10^3$ | NUMBER OF COLONIES |
| --- | --- | --- |
| T98G-sense | 3 | 305 |
| T98G-antisense | 3 | 5 |
| C6 | 3 | 280 |
| C6-sense | 3 | 230 |
| C6-antisense | 3 | 115 |

Cells were seeded at the indicated densities and colonies were counted after 14 days in culture. Both cell lines showed a consistently higher efficiency of colony formation than t-antigen transfected mouse embryo cells.

The T98G cells used are lines which have been stably transfected with a heat shock promoter construct which transcribes either a sense or antisense transcript for the first 309 bp of the IGF-1 receptor. The T98G cells containing the antisense construct grew at 40–50% of the rate of the lines containing the sense construct.

The C6 cell line was treated with 80 μg/ml of antisense oligonucleotide to the IGF-1 receptor known to reduce the level of IGF-1 receptor at the cell surface (Pietrzkowski, et al., *Cell Growth and Diff.,* 1992, 3:199). The sequence used corresponds to the first 18 bp after the ATG initiation codon of the IGF-1 receptor cDNA, the addition of the antisense oligonucleotide had very little effect on the anchorage dependent growth of these cells in 10% serum.

An additional experiment was performed to show that the ability of SVLT to transform fibroblasts depends directly on the presence of functional IGF-1 receptor. This experiment was based on the observation that cells expressing IGF-1 receptor constitutively are able to grow in serum-free medium supplemented with IGF-1 or insulin at supraphysiological concentrations (Pietrzkowski, et al., *Cell Growth and Diff.,* 1992, 3:199, McCubrey, et al., *Blood,* 1991, 78:921). Thus, one of the (tsA)R- clones was transfected with a plasmid (Cvn-IGF-1 receptor) expressing the full-length coding sequence of human Igf1r cDNA and also the neomycin-resistance gene, both under the control of the SV40 promoter (Ullrich, et al., *EMBO J,* 1986, 5:2503). Clones selected directly in serum-free medium supplemented with insulin (20 μg/ml) were picked; under these conditions, only clones constitutively expressing the IGF-1 receptor can grow (Pietrzkowski, et al., supra). By autophosphorylation analysis, these clones expressed IGF-1 receptor at levels comparable to those of Balb/c 3T3 cells. these clones were able to form colonies efficiently in soft agar, without the addition of IGF-1. The endogenously-produced T antigen, which was previously ineffective, attained its transforming potential once the cells acquired constitutively-expressed human IGF-1 receptor.

Example 12

Immunostaining for Large T Antigen

Cells fixed in cold methanol were incubated with a 1:10 dilution of anti-large T antigen antibody (PAb 419; Oncogene Science, Uniondale, N.Y.) then stained with a 1:100 dilution of a fluorescinated goat antimouse immunoglobulin G antibody (Oncogene Science). Staining intensity was measured in arbitrary units by computer analysis of photographic images of the stained cells.

Example 13

Soft Agar Assay

Anchorage-independent growth was assayed by scoring the number of colonies formed in 0.2% agarose (with either a 1% or 0.4% agarose underlay). T antigen transfected cells were allowed to grow for three weeks while glioblastoma cell colonies were counted after two weeks due to the higher growth rate of these cells relative to the T antigen-transformed cells.

Previous indirect data, showing that NIH 3T3 cells over-expressing IGF-1 receptor grow in soft agar in the presence of the ligand (Kaleko, et al., *Mol. Cell. Biol.*, 1990, 10:464) and that the tumorigenicity of the rat glioblastoma C6 cell line is abrogated by antisense Igf-1 RNA (Trojan et al., supra) are consistent with the results obtained with mutant cells lacking IGF-1 receptor. These results suggest that IGF-1 receptor mediates signaling of IGF-1 is an indispensable component of the operation of a transformation pathway. To show that this is the case, an antisense RNA strategy was performed with C6 cells and also with cells of an additional glioblastoma cell line, T98G (Stein, supra), which grow well in 1% serum.

T98G glioblastoma cells were transfected with appropriate constructs, to derive cell lines expressing either antisense or (control) sense human Igf1r RNA. Soft agar assays using these derivatives showed that, in comparison to the control cells, the number of colonies formed by 98G cells expressing Igf1r antisense RNA was reduced more than 60-fold, see TABLE 6. In an analogous experiment, C6 cell colony formation in soft agar was reduced 2-fold in the presence of an antisense oligodeoxynucleotide inhibiting Ig1fr mRNA, see TABLE 6. The growth of C6 cells in culture dishes was not reduced more than 10% in the presence of the same concentration of antisense oligodeoxynucleotides, while the growth rate of T98G cells expressing antisense RNA was 40% of that of wild-type cells or cells expressing sense RNA. These observations suggest that the transformation phenotype is more sensitive to the abrogation or diminution of IGF-1 receptor function than the inhibition of growth.

Example 14

Cross-Linking of IGF-1 Receptor

Radioiodinated IGF-1 was cross-linked to the IGF-1 receptor using disuccinimidyl suberate as described by Yamori, et al., *Cancer Res.*, 1991, 51, 5859. After cross-linking, the proteins were resolved on an 8% polyacrylamide gel and the dried gel exposed to X-ray film (Kodak X-OMAT) for autoradiography.

Example 15

Antisense Oligonucleotides

The antisense and sense oligodeoxynucleotides to the IGF-1 receptor mRNA used for the colony formation assay of C6 cells were prepared according to Pietrzkowski, et al., *Cell Growth and Diff.*, 1992, 3, 199. They correspond to the 18 bp sequence following the ATG of the IGF-1 receptor cDNA. The antisense oligonucleotides were added to the cells at the time of seeding at a concentration of 80 μg/ml.

Example 16

In Vivo Experiments Performed in Rats

Three C6 cell lines were prepared. C6 cell lines were separately transfected with expression vectors capable of expressing sense or antisense oligonucleotides, respectively, to IGF-1 receptor RNA. Plasmids were prepared as described above. Wild type or untransfected C6 cells were also grown in culture. Cell lines were established by transfection of C6 with HSP70 promoter driving 305 bp of IGF-1 receptor RNA cell lines established by transfection. The cells carried a neomycin resistance gene. The cells were selected with G418 and monitored for IGF-1 receptor expression.

Rats were subcutaneously injected in the flank, i.e. side, with one of the three C6 rat glioblastoma cell lines at a concentration of $10^7$. This tumor grows vigorously in rats, reaching large sizes and eventually killing the animals. Rats injected with wild type cells resulted in tumors of about 1–2 cm.

Tumors resulted in rats injected with wild type cells and with cells expressing sense oligonucleotides, 27/27 rats injected with wild type cells and 12/12 rats injected with sense oligonucleotides, see TABLE 7. However, none of the 24 rats injected with antisense oligonucleotides yielded tumors, see TABLE 7.

In another experiment, animals were first injected with cells expressing sense oligonucleotides, prepared as set forth above, at a concentration of $10^7$. Six days later, the same animals were injected with wild type cells, at a concentration of $10^7$, and 6 of the 6 rats resulted in bilateral tumor development. None of the rats injected with antisense oligonucleotides initially and then wild type cells resulted in tumor development, see TABLE 7.

Another experiment injected wild type and sense expressing cells simultaneously, or wild type and antisense simultaneously. All of the rats given sense oligonucleotides (3/3) revealed tumors while 0/3 of the rats receiving antisense oligonucleotides had tumor development, see TABLE 7.

In anther experiment, fifteen rats were injected with wild type cells initially followed two weeks later with antisense oligonucleotides. Autopsies revealed (all injection concentrations were $10^7$ cells) complete tumor regression; the tumors disappeared. Significantly, the antisense oligonucleotides were injected into the flank opposite the wild type injection, TABLE 7.

TABLE 7

Effect of IGF-1R Sense and Antisense RNA on Tumor Induction in Rats

| Injection #1 (right) | Injection #2 (left) | Tumor Development number of animals |
|---|---|---|
| Wild-sense | n/a | 27/27 |
| Sense | n/a | 12/12 |
| Antisense | n/a | 0/24 |
| Sense | Wild-type (day 6) | 6/6 bilaterally |
| Antisense | Wild-type (day 6) | 0/6 |
| Wild-type | Sense (simultaneous) | 3/3 bilaterally |

TABLE 7-continued

Effect of IGF-1R Sense and Antisense RNA on Tumor Induction in Rats

| Injection #1 (right) | Injection #2 (left) | Tumor Development number of animals |
| --- | --- | --- |
| Wild-type | Antisense (simultaneous) | 0/3 |
| Wild-type | Antisense (2 weeks) | complete tumor regression in right flank, 15/15 |

The data resulting from the in vivo rat experiments identified above is significant for application to human cancers. The rat tumors in the above identified experiments were syngeneic. The tumors originated in these rats, the tumors are not foreign and the data is therefore the data is not the result of rejection of these tumors by the rats.

Various modifications of the invention in addition to those shown and described herein will be apparent to those skilled in the art from the foregoing description. Such modifications are also intended to fall within the scope of the appended claims.

---

What is claimed is:

1. An antisense oligonucleotide comprising SEQ ID NO:4.

2. An antisense oligonucleotide comprising a sequence substantially complementary to codons −29 to −24 of the signal sequence of the IGF-1 receptor.

3. A pharmaceutical composition comprising a therapeutically effective amount of an antisense oligonucleotide of claim 1 and a pharmaceutically acceptable carrier.

4. An antisense oligonucleotide comprising SEQ ID NO:8.

5. An antisense oligonucleotide comprising an oligonucleotide sequence complementary to codons 1 to 309 of the sequence of the IGF-1 receptor.

6. An expression vector comprising an antisense sequence complementary to codons 1 to 309 of the sequence of the IGF-1 receptor.

7. A pharmaceutical composition comprising a therapeutically effective amount of an antisense oligonucleotide of claim 4 and a pharmaceutically acceptable carrier.

8. An oligonucleotide which is substantially complementary to a region of insulin-like growth factor 1 receptor RNA, wherein said oligonucleotide inhibits cancer cell proliferation in a soft agar assay and is at least 18 nucleotides in length.

9. An oligonucleotide which is substantially complementary to the region consisting of the first 309 base pairs of the coding sequence of insulin-like growth factor 1 receptor RNA, or fragment thereof, wherein said oligonucleotide inhibits cancer cell proliferation in a soft agar assay.

10. An oligonucleotide which is substantially complementary to a portion of the signal sequence of insulin-like growth factor 1 receptor RNA, wherein said oligonucleotide inhibits cancer cell proliferation in a soft agar assay.

11. The oligonucleotide of claim 8 wherein said oligonucleotide comprises at least one phosphorothioate linkage.

12. An expression vector capable of expressing an oligonucleotide which is substantially complementary to a region of insulin-like growth factor 1 receptor RNA and which is at least 18 nucleotides in length, wherein said oligonucleotide inhibits cancer cell proliferation in a soft agar assay.

13. An expression vector capable of expressing an oligonucleotide which is substantially complementary to the region consisting of the first 309 base pairs of the coding sequence of insulin-like growth factor 1 receptor RNA, or fragment thereof, and wherein said oligonucleotide inhibits cancer cell proliferation in a soft agar assay.

14. An expression vector capable of expressing an oligonucleotide which is substantially complementary to a portion of the signal sequence of insulin-like growth factor 1 receptor RNA, and wherein said oligonucleotide inhibits cancer cell proliferation in a soft agar assay.

15. A composition comprising the oligonucleotide of claim 8 and a pharmaceutically acceptable carrier.

16. A composition comprising the oligonucleotide of claim 9 and a pharmaceutically acceptable carrier.

17. A composition comprising the oligonucleotide of claim 10 and a pharmaceutically acceptable carrier.

18. A composition comprising an expression vector and a pharmaceutically acceptable carrier, wherein said expression vector is capable of expressing an oligonucleotide which is substantially complementary to a region of insulin-like growth factor 1 receptor RNA, wherein said oligonucleotide inhibits cancer cell proliferation in a soft agar assay.

19. A composition comprising the expression vector of claim 13 and a pharmaceutically acceptable carrier.

20. A composition comprising the expression vector of claim 14 and a pharmaceutically acceptable carrier.

21. An expression vector capable of expressing an oligonucleotide comprising SEQ ID NO:4, wherein said oligonucleotide inhibits cancer cell proliferation in a soft agar assay.

\* \* \* \* \*